US009913632B2

(12) United States Patent
Mamiya et al.

(10) Patent No.: US 9,913,632 B2
(45) Date of Patent: Mar. 13, 2018

(54) PUNCTURE NEEDLE FOR ENDOSCOPE

(71) Applicant: OLYMPUS CORPORATION, Hachioji-shi, Tokyo (JP)

(72) Inventors: Tomohiko Mamiya, Kawasaki (JP); Kiyotaka Matsuno, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/256,041

(22) Filed: Sep. 2, 2016

(65) Prior Publication Data

US 2016/0367233 A1 Dec. 22, 2016

Related U.S. Application Data

(63) Continuation of application No. PCT/JP2015/072490, filed on Aug. 7, 2015.

(30) Foreign Application Priority Data

Aug. 7, 2014 (JP) .................. 2014-161578

(51) Int. Cl.
| | |
|---|---|
| *A61B 10/04* | (2006.01) |
| *A61B 1/00* | (2006.01) |
| *A61B 8/12* | (2006.01) |
| *A61B 1/05* | (2006.01) |
| *A61B 8/08* | (2006.01) |
| *A61B 8/00* | (2006.01) |

(52) U.S. Cl.
CPC ................ *A61B 10/04* (2013.01); *A61B 1/00* (2013.01); *A61B 1/05* (2013.01); *A61B 8/0841* (2013.01); *A61B 8/12* (2013.01); *A61B 8/4461* (2013.01); *A61B 2010/045* (2013.01)

(58) Field of Classification Search
CPC ................................. A61B 2010/045
See application file for complete search history.

(56) References Cited

U.S. PATENT DOCUMENTS 4,982,727 A * 1/1991 Sato .................. A61B 17/29
600/104
5,601,588 A * 2/1997 Tonomura .............. A61B 10/04
606/181

(Continued)

FOREIGN PATENT DOCUMENTS

| JP | H08-150145 A | 6/1996 |
|---|---|---|
| JP | H11-128233 A | 5/1999 |

(Continued)

OTHER PUBLICATIONS

Nov. 2, 2015 Search Report issued in International Patent Application No. PCT/JP2015/072490.

*Primary Examiner* — Daniel Cerioni
*Assistant Examiner* — Yasmeen S Warsi
(74) *Attorney, Agent, or Firm* — Oliff PLC

(57) ABSTRACT

In a puncture needle for an endoscope, in a state in which a distal end of an outer sheath is located in an observation field of an observation optical system of an endoscope and a needle slider is retracted to abut a needle slider engaging section, a distal end of an inner sheath is located closer to a distal side than a proximal end of a raising base in the outer sheath, and a proximal end of the inner sheath is located closer to a proximal side than a needle tip of a needle tube in the outer sheath.

19 Claims, 11 Drawing Sheets

(56) References Cited

U.S. PATENT DOCUMENTS

| | | | |
|---|---|---|---|
| 2012/0170970 A1* | 7/2012 | Kitagawa | A61B 1/0011 403/81 |
| 2012/0197119 A1* | 8/2012 | Takachi | A61B 10/04 600/439 |
| 2013/0184732 A1 | 7/2013 | Tanaka et al. | |

FOREIGN PATENT DOCUMENTS

| | | |
|---|---|---|
| JP | 2001-120557 A | 5/2001 |
| JP | 2013-144012 A | 7/2013 |

* cited by examiner

PUNCTURE NEEDLE FOR ENDOSCOPE

This application is a continuation application, based on PCT/JP2015/072490, filed on Aug. 7, 2015, claiming priority based on Japanese Patent Application No. 2014-161578, filed in Japan on Aug. 7, 2014, the contents of the PCT application and the Japanese Patent Application are incorporated herein by reference.

FIELD OF THE INVENTION

The present invention relates to a puncture needle for an endoscope.

DESCRIPTION OF THE RELATED ART

In the related art, an inspection method that is referred to as a biopsy of collecting a small amount of body tissue and observing the body tissue microscopically is known. When tissue of a deep part of an organ or the like is collected, since observation by an optical endoscope becomes difficult, an ultrasonogram of the organ is acquired by an ultrasonic endoscope or the like, and a puncture needle having a cylindrical needle tube is inserted into the organ to collect the tissue under ultrasonic observation (for example, see Japanese Unexamined Patent Application, First Publication No. 2001-120557).

In the above-mentioned puncture needle, the needle tube is disposed in a sheath that can be inserted into a treatment tool channel of an ultrasonic endoscope or the like, and an inner surface of the treatment tool channel is prevented from damage by a sharp distal end of the needle tube.

SUMMARY OF INVENTION

Means for Solving the Problem

An aspect of the present invention is a puncture needle for an endoscope used with an endoscope having a treatment tool insertion channel, a raising base configured to raise a treatment tool inserted through the channel, and an observation optical system, the puncture needle for an endoscope including: a coil sheath having an outer diameter that is capable of being inserted into the treatment tool insertion channel and constituted by a wire wound as a coil shape along a longitudinal axis thereof; a needle tube having a needle tip formed at a distal end thereof and movable along the longitudinal axis of the coil sheath inside the coil sheath; a manipulation section provided at a proximal portion of the coil sheath; a needle slider disposed at the manipulation section and configured to advance and retract the needle tube by advance and retract manipulation with respect to the manipulation section; a needle slider engaging section disposed at the manipulation section and abutting the needle slider when the needle slider is retracted to a proximal side; and an inner sheath having a distal end, a proximal end, an outer circumferential surface configured to cover a gap between neighboring loops of the wire of the coil sheath between the distal end and the proximal end inside of the coil sheath, and an inner circumferential surface configured to form an insertion path in which the needle tube is capable of being inserted, wherein, in a state in which a distal end of the coil sheath is located in an observation field of the observation optical system and the needle slider is retracted to abut the needle slider engaging section, the distal end of the inner sheath is located closer to a distal side than a proximal end of the raising base in the coil sheath, and the proximal end of the inner sheath is located closer to a proximal side than a needle tip of the needle tube in the coil sheath.

The distal end of the inner sheath may be fixed to the distal end of the coil sheath. The inner sheath may be slidable with respect to the coil sheath in the entire region closer to a proximal side than a fixed place of the distal end of the coil sheath to the inner sheath.

The coil sheath may have a metal coil body through which the inner sheath and the needle tube are inserted; a tubular distal tip fixed to a distal end of the coil body, having an inner diameter smaller than that of the coil body and through which the needle tube is capable of being inserted; and a protrusion protruding further inward than an inner surface of the coil body at a position distant from the distal end of the coil body to the proximal side, and the inner sheath may be disposed between the distal tip and the protrusion and advance and retract movement in a direction along a centerline of the coil body may be restricted by the distal tip and the protrusion.

The coil body may be a coil having a metal wire that are exposed to an outer surface of the coil sheath, and the inner sheath may be attached to an inner surface of the coil body to cover the inner surface of the coil body throughout the circumference when seen in a cross-section perpendicular to the centerline of the coil body.

The raising base may come in contact with the coil sheath at the distal end of the channel to deflect the distal end of the coil sheath.

The endoscope may have a bendable section in which a plurality of joints configured to bend the channel are connected, and which is formed closer to the proximal side than the raising base.

The inner sheath may have a distal region raised by the raising base, the distal region may have a fixing section fixed to the coil sheath, a region of the inner sheath closer to a proximal side than the fixing section may be relatively movable with respect to the coil sheath, and when the proximal end of the inner sheath is moved to a distal side of the coil sheath according to raising of the coil sheath by the raising base, the proximal end of the inner sheath may be located closer to the proximal side than the needle tip of the needle tube in the coil sheath.

The inner sheath may have a proximal region extending closer to the proximal side of the coil sheath than the needle tip of the needle tube, the proximal region may have a fixing section fixed to the coil sheath, a region of the inner sheath closer to the distal side than the fixing section may be relatively movable with respect to the coil sheath, and when the distal end of the inner sheath is moved to the proximal side of the coil sheath according to raising of the coil sheath by the raising base, the distal end of the inner sheath may be located closer to the distal side than the proximal end of the raising base in the coil sheath.

The inner sheath may have an intermediate region disposed between the needle tip of the needle tube and the proximal end of the raising base, the intermediate region may have a fixing section fixed to the coil sheath, in the inner sheath, a region closer to the distal side and a region closer to the proximal side than the fixing section may be relatively movable with respect to the coil sheath, and when the distal end of the inner sheath is moved to the proximal side of the coil sheath according to raising of the coil sheath by the raising base and the proximal end of the inner sheath is moved to the distal side of the coil sheath, the distal end of the inner sheath may be located closer to the distal side than the proximal end of the raising base in the coil sheath, and the proximal end of the inner sheath may be located closer to the proximal side than the needle tip of the needle tube in the coil sheath.

DETAILED DESCRIPTION OF THE INVENTION

First Embodiment

Figure 1:
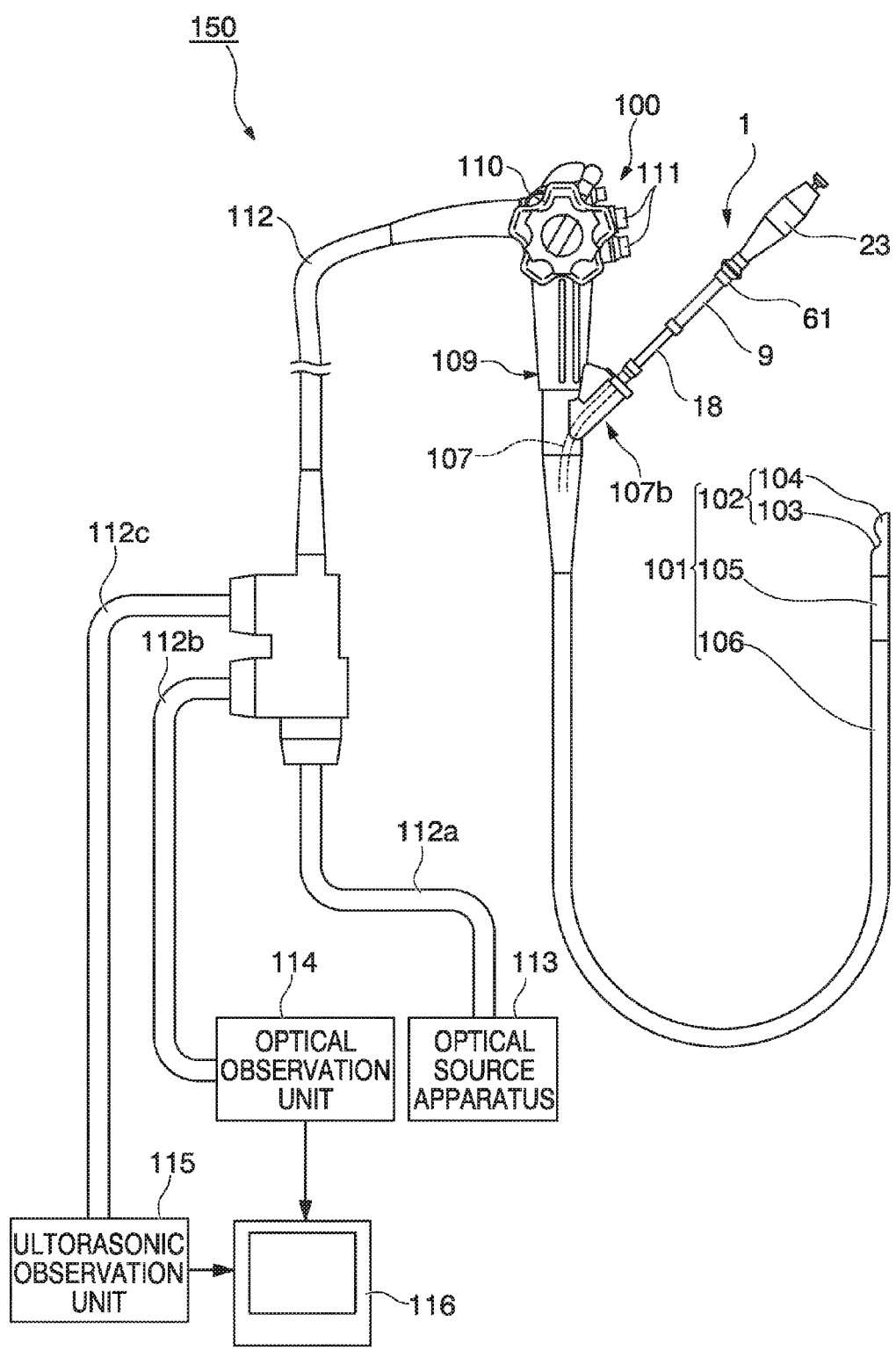
FIG. 1 is a general view of a biopsy system including a puncture needle for an endoscope of a first embodiment of the present invention.
Figure 2:
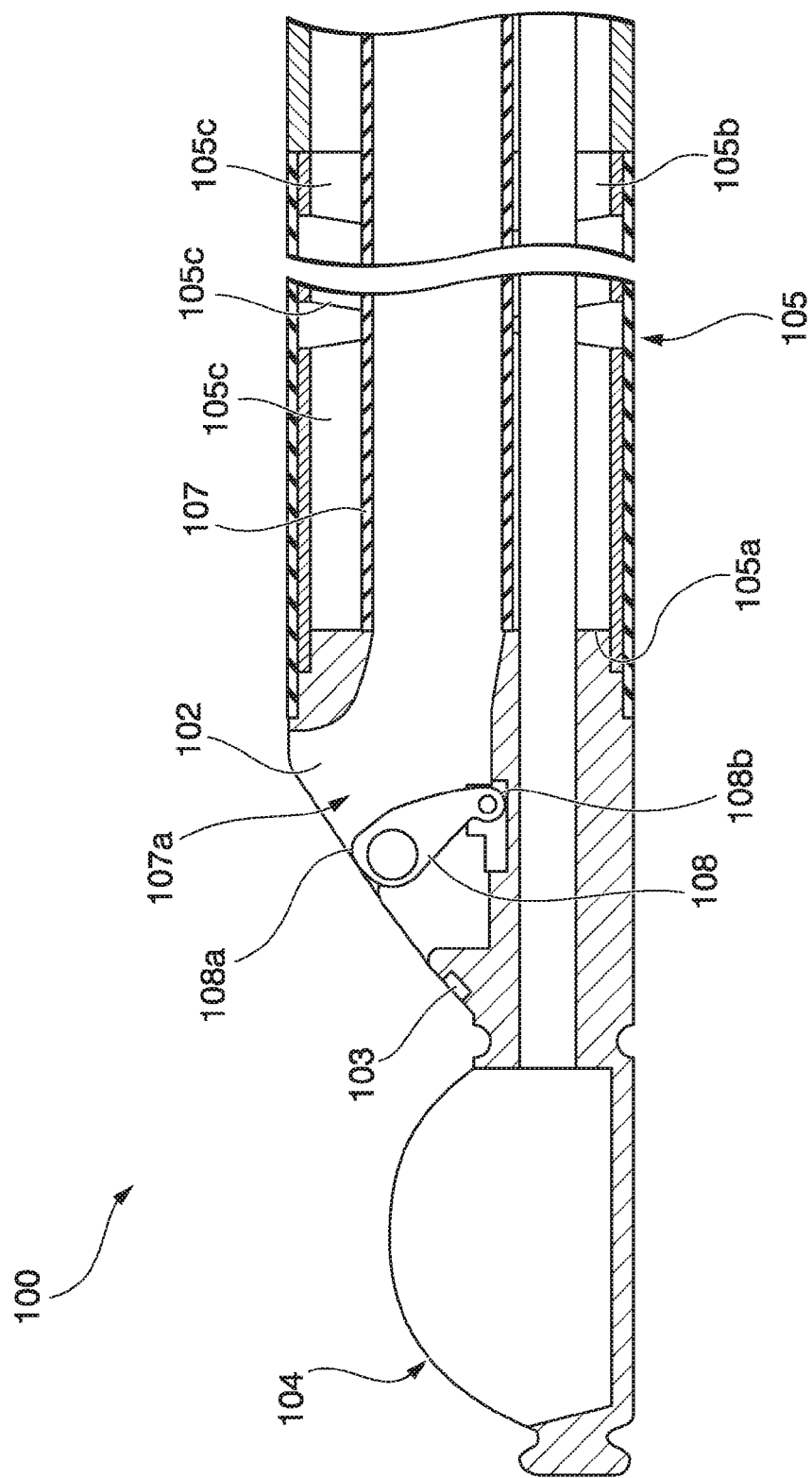
FIG. 2 is a cross-sectional view of a distal portion of an ultrasonic endoscope of the biopsy system.
Figure 3:
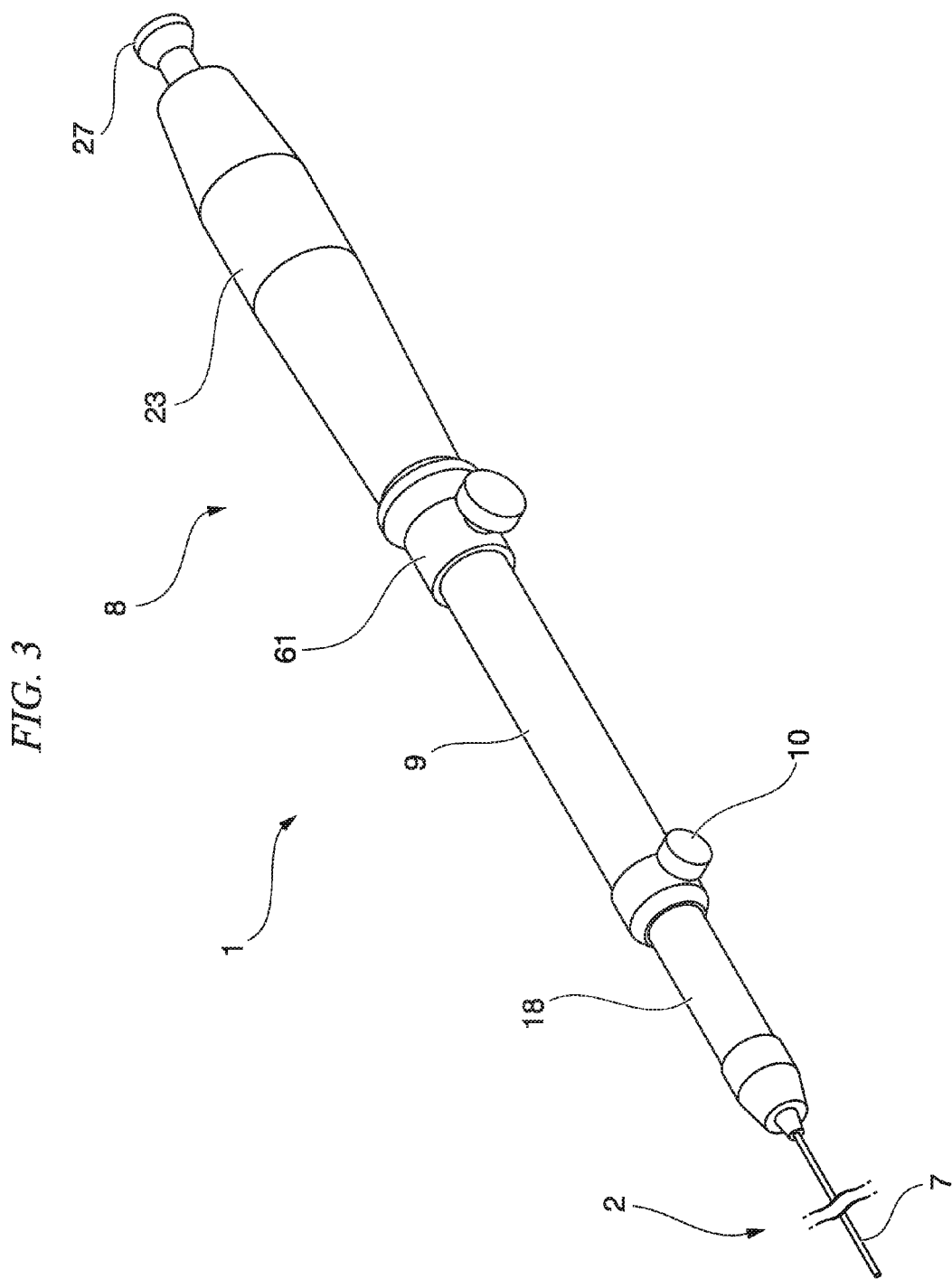
FIG. 3 is a perspective view of the puncture needle for an endoscope of the embodiment.
Figure 4:
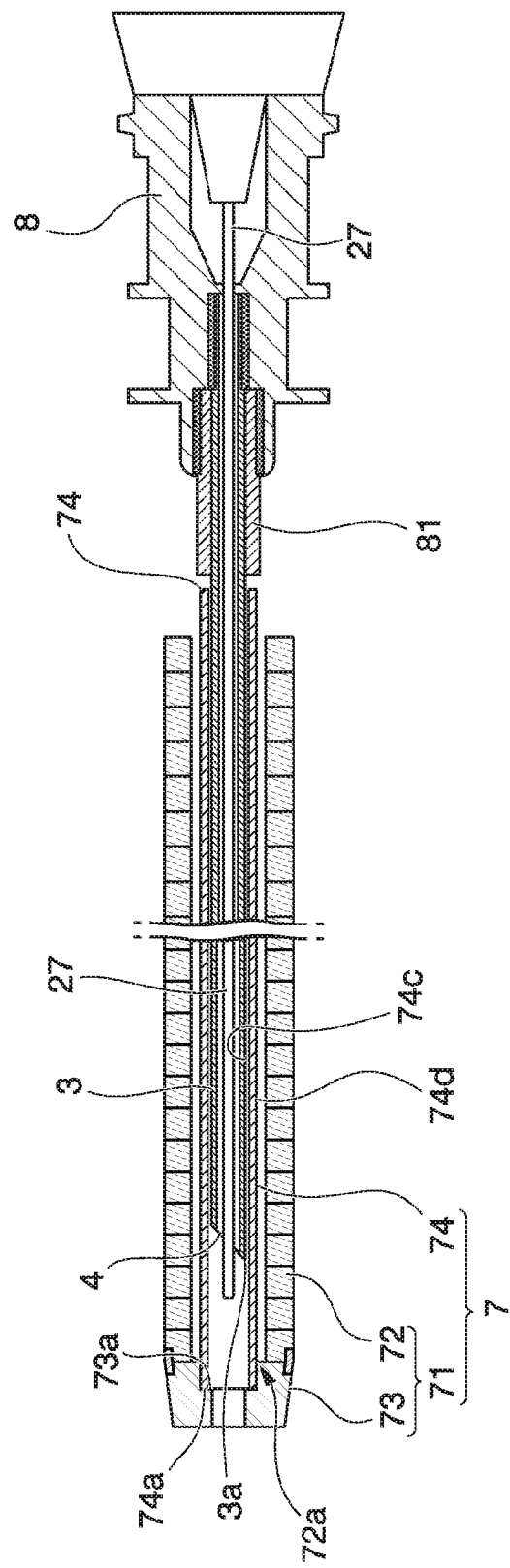
FIG. 4 is a cross-sectional view of a distal portion of the puncture needle for an endoscope.

A first embodiment of the present invention will be described by exemplifying a biopsy system including a puncture needle for an endoscope of the embodiment. FIG. 1 is a general view of a biopsy system including a puncture needle for an endoscope of the embodiment. FIG. 2 is a cross-sectional view of a distal portion of an ultrasonic endoscope of the biopsy system of the embodiment. FIG. 3 is a perspective view of the puncture needle for an endoscope. FIG. 4 is a cross-sectional view of a distal portion of the puncture needle for an endoscope.

A biopsy system 150 of the embodiment shown in FIG. 1 is a medical instrument that can be used in a biopsy of collecting tissue in a body. The biopsy system 150 includes an ultrasonic endoscope 100 and a puncture needle for an endoscope 1 (hereinafter, simply referred to as "the puncture needle 1").

As shown in FIG. 1, the ultrasonic endoscope 100 includes an insertion section 101 inserted into a body from a distal end thereof, an operation section 109 attached to a proximal end of the insertion section 101, a universal cord 112 having a first end connected to a side portion of the operation section 109, a light source apparatus 113 connected to a second end of the universal cord 112 via a branch cable 112a, an optical observation unit 114 connected to the second end of the universal cord 112 via a branch cable 112b, and an ultrasonic observation unit 115 connected to the second end of the universal cord 112 via a branch cable 112c.

The insertion section 101 has a distal hard section 102, a bendable section 105 and a flexible tube section 106 that are formed sequentially from a distal side thereof.

As shown in FIGS. 1 and 2, the distal hard section 102 includes an optical imaging mechanism (an observation optical system) 103 configured to perform optical observation, an ultrasonic scanning mechanism 104 configured to perform ultrasonic observation, and a raising base 108 configured to raise a treatment tool inserted through a treatment tool insertion channel 107, which will be described below, and the raising base 108 is disposed at a position far from a distal end of the bendable section 105.

The optical imaging mechanism 103 includes various constitutions (not shown) such as an optical imaging system in which a field of vision is directed toward an inclined forward side of the distal hard section 102, and an image sensor such as a CCD, a CMOS, or the like, configured to detect an image of a subject that is introduced through the optical imaging system, and a CPU or the like configured to control operation of the image sensor.

The ultrasonic scanning mechanism (a probe) 104 includes an ultrasonic vibrator (not shown) configured to emit and receive ultrasonic waves. The ultrasonic waves which are emitted from the ultrasonic vibrator, hit an observation target, and reflected off the target are received by the ultrasonic vibrator of the ultrasonic scanning mechanism 104. The ultrasonic scanning mechanism 104 outputs a signal to the ultrasonic observation unit 115 based on the ultrasonic waves received by the ultrasonic vibrator. The ultrasonic scanning mechanism 104 of the embodiment is used to acquire an ultrasonic wave image of the tissue serving as the biopsy target and acquire an ultrasonic wave image of a needle tube 3 in a process of a procedure of the biopsy.

The raising base 108 shown in FIG. 2 is a member configured to deflect (raise) a distal portion of a sheath 7 of the puncture needle 1 into a direction crossing a centerline of the insertion section 101. The raising base 108 is a member having a distal end 108a and a proximal end 108b and extending from the proximal end 108b toward the distal end 108a. A distal end of the channel 107 is opened at the distal end 108a of the raising base 108. The raising base 108 can be pulled by a raise wire (not shown) extending to the operation section 109 in the operation section 109 so as to be raised position. As the raise wire is pulled, the distal end 108a of the raising base 108 is pivoted about the proximal end 108b of the raising base 108, and thus, an outer surface of the sheath 7 disposed on the raising base 108 can be pressed to bend (raise) the sheath 7.

The bendable section 105 is a tubular member constituted by a plurality of joints 105c having a tubular shape and connected in parallel in a centerline direction of the insertion section 101. The bendable section 105 is a bendable section bent in a predetermined direction by pulling an angle wire (not shown) fixed to a distal end 105a (see FIG. 2) of the bendable section 105 and extending to the operation section 109 in the operation section 109. The bendable section 105 of the embodiment can be bent in two directions along a scanning direction of ultrasonic waves.

Either of the raising base 108 or the bendable section 105 is a bending applying mechanism configured to deform the puncture needle 1 serving as a treatment tool of the embodiment in a bent shape according to bending manipulation by the operation section 109.

The flexible tube section 106 is a tubular member flexibly formed such that the distal hard section 102 in a lumen tissue or a body cavity can be guided to a predetermined position.

The channel 107 and a pipeline (not shown) configured to perform air supply and water supply, suction, or the like, are formed in either of the bendable section 105 and the flexible tube section 106.

The channel 107 shown in FIGS. 1 and 2 is a tubular section through which the puncture needle 1 can be inserted.

A distal end of the channel 107 is opened at the distal end 108a of the raising base 108 of the distal hard section, and a proximal end of the channel 107 is opened at a side surface of a distal side of the operation section 109. In a process in which the sheath 7 of the puncture needle 1 protrudes from the distal end of the channel 107, the raising base 108 can come in contact with an outer surface of the sheath 7 of the puncture needle 1. A proximal port member 107b formed in a flange shape is fixed to the proximal end of the channel 107. The puncture needle 1 used with the ultrasonic endoscope 100 can be fixed to the proximal port member 107b.

The operation section 109 shown in FIG. 1 has an outer surface formed such that an operator who uses the ultrasonic endoscope 100 can hold the operation section with his/her hand. The operation section 109 includes a bending manipulation mechanism 110 configured to pull an angle wire to bend the bendable section 105 or pull a raise wire to operate the raising base 108, and a plurality of switches 111 configured to perform air supply, water supply or suction through the pipeline.

The light source apparatus 113 is an apparatus configured to emit illumination light for imaging using the optical imaging mechanism 103.

The optical observation unit 114 is configured to project pictures imaged by the image sensor of the optical imaging mechanism 103 on a monitor 116.

The ultrasonic observation unit 115 is configured to receive a signal output from the ultrasonic scanning mechanism 104 and generate an image based on the signal to project the image on the monitor 116.

Next, a configuration of the puncture needle 1 of the embodiment will be described.

As shown in FIG. 3, the puncture needle 1 includes an insertion body 2, a manipulation section 8 and a stylet 27.

The insertion body 2 is an elongated member that can be inserted through the channel 107 of the ultrasonic endoscope 100 shown in FIG. 1.

As shown in FIGS. 3 and 4, the insertion body 2 includes the needle tube 3 and the sheath 7.

The needle tube 3 is a tubular member having a distal end and a proximal end and is manipulated by the manipulation section 8 of the puncture needle 1 to advance and retract.

A material of the needle tube 3 may be a material having flexibility and elasticity such that the needle tube 3 can easily return to a linear state even when curved by an external force. For example, the material of the needle tube 3 may be an alloy material such as a stainless steel alloy, a nickel titanium alloy, a cobalt chromium alloy, or the like.

The distal end of the needle tube 3 has a needle tip 3a that is sharply formed to cause the needle tube 3 to puncture the tissue, and an opening 4 serving as an inlet into which the tissue enters the needle tube 3.

The opening 4 formed at the distal end of the needle tube 3 is formed by obliquely cutting the distal end of the tubular member that forms the needle tube 3 with respect to the distal end, and is sharply formed such that the opening 4 can enter the living body tissue. A specific shape of the opening 4 may be appropriately selected from known various shapes in consideration of tissue or the like serving as a target.

As shown in FIG. 4, the sheath 7 includes an outer sheath 71 and an inner sheath 74.

The outer sheath 71 includes a coil body 72 in which a metal wire is wound in a coil shape with loops around a longitudinal axis serving as a central axis, and a tubular distal tip 73 fixed to a distal end of the coil body 72. In addition, the coil body 72 has a distal end and a proximal end, an outer diameter that can be inserted into the channel 107 between the distal end and the proximal end, and an internal space 72a from which the longitudinal axis extends.

The wire that constitute the coil body 72 may be formed of a material appropriately selected from a stainless steel, a shape-memory alloy, a super-elastic alloy, and so on, and may have a shape appropriately selected from a circular cross section, a rectangular cross section, and so on, in consideration of bending easiness or a restoring force of the coil body 72.

The distal tip 73 is a tubular member fixed to a distal surface of the coil body 72 and having a through-hole through which the needle tube 3 can be inserted. An inner diameter of the distal tip 73 may be larger than that of the inner sheath 74, which will be described below. When the inner diameter of the distal tip 73 is larger than that of the inner sheath 74, the needle tube 3 disposed in the inner sheath 74 is located at a position separated from the inner surface of the distal tip 73, and a frictional resistance is reduced in comparison with the case in which the needle tube 3 slides with respect to the inner surface of the distal tip 73 with continuous contact on the inner surface of the distal tip 73.

As shown in FIG. 4, the inner sheath 74 is a tubular member formed of a resin and having a distal end 74a and a proximal end. The inner sheath 74 is disposed coaxially with a central axis of the coil body 72 in the internal space 72a of the coil body 72. In addition, the inner sheath 74 has an inner circumferential surface 74c and an outer circumferential surface 74d, the inner circumferential surface 74c forms an insertion path into which the needle tube 3 can be inserted, and the outer circumferential surface 74d is disposed over the neighboring loops of the wire of the coil body 72 between the distal end 74a and the proximal end of the inner sheath 74 in the internal space 72a of the coil body 72. The outer circumferential surface 74d covers a gap between the loops of the wire generated when the coil body 72 is bent between the distal end 74a and the proximal end of the inner sheath 74 from the inside of the coil body 72. For this reason, the inner sheath 74 functions as a cover member with respect to the coil body 72. The distal end 74a of the inner sheath 74 is fixed to the distal tip 73. The proximal end of the inner sheath 74 extends to the operation section 109.

In the entire length of the inner sheath 74, the inner sheath 74 is freely slidable with respect to the outer sheath 71 at a closer side relative to a fixing place of the distal end 74a of the inner sheath 74 and the distal tip 73.

Figure 5:
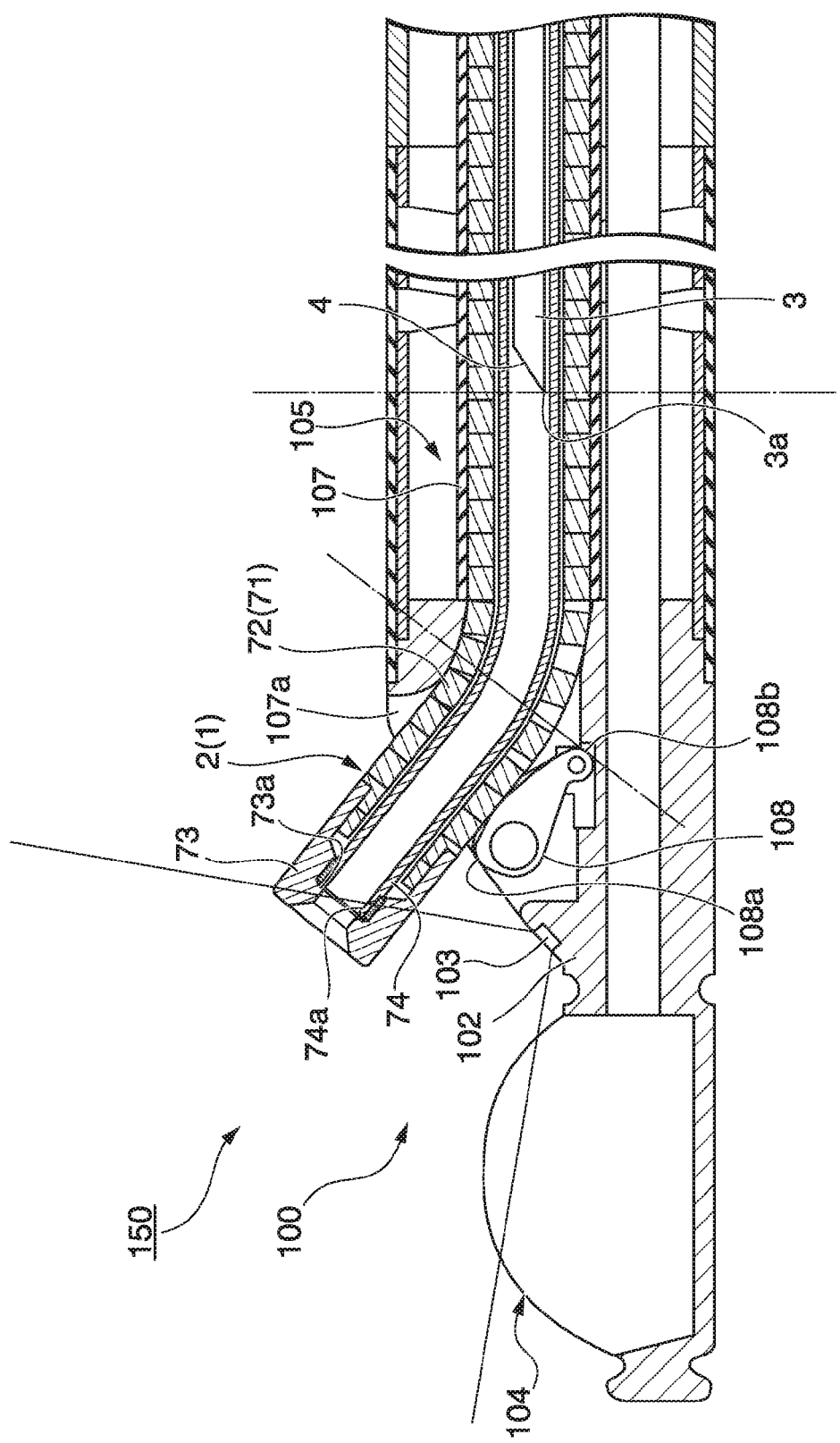
FIG. 5 is a cross-sectional view showing a state in which the puncture needle for an endoscope is combined with an endoscope.

As shown in FIG. 5, the distal end of the inner sheath 74 is located closer to the distal side than the proximal end 108b of the raising base 108 in the internal space 72a of the coil body 72 in a state in which the distal end of the coil body 72 is located in an observation field of an optical observation unit 114 of the ultrasonic endoscope 100 and a needle slider (to be described below) is moved to a position abutting a needle slide engaging section. In addition, in the same state, the proximal end of the inner sheath 74 is located closer to a proximal side than the needle tip 3a of the needle tube 3 in the internal space 72a of the coil body 72. Further, in the embodiment, the proximal end of the inner sheath 74 extends to the vicinity of the manipulation section 8. According to a positional relation, since the inner sheath 74 is disposed in a moving region of the needle tip 3a of the needle tube 3 in the internal space 72a of the coil body 72 bent by the raising base 108 or the bendable section 105, the needle tip 3a of the needle tube 3 can be prevented from being caught in the gap between the loops of the wire of the coil body 72 bent by the raising base 108 or the bendable section 105.

The manipulation section 8 shown in FIGS. 1 and 3 includes a manipulation main body 9 disposed at the proximal portion of the sheath 7, an attachment adaptor 18 connected to the manipulation main body 9, and a needle slider 23 connected to the proximal portion of the needle tube 3 at the proximal side of the manipulation main body 9.

Figure 7:
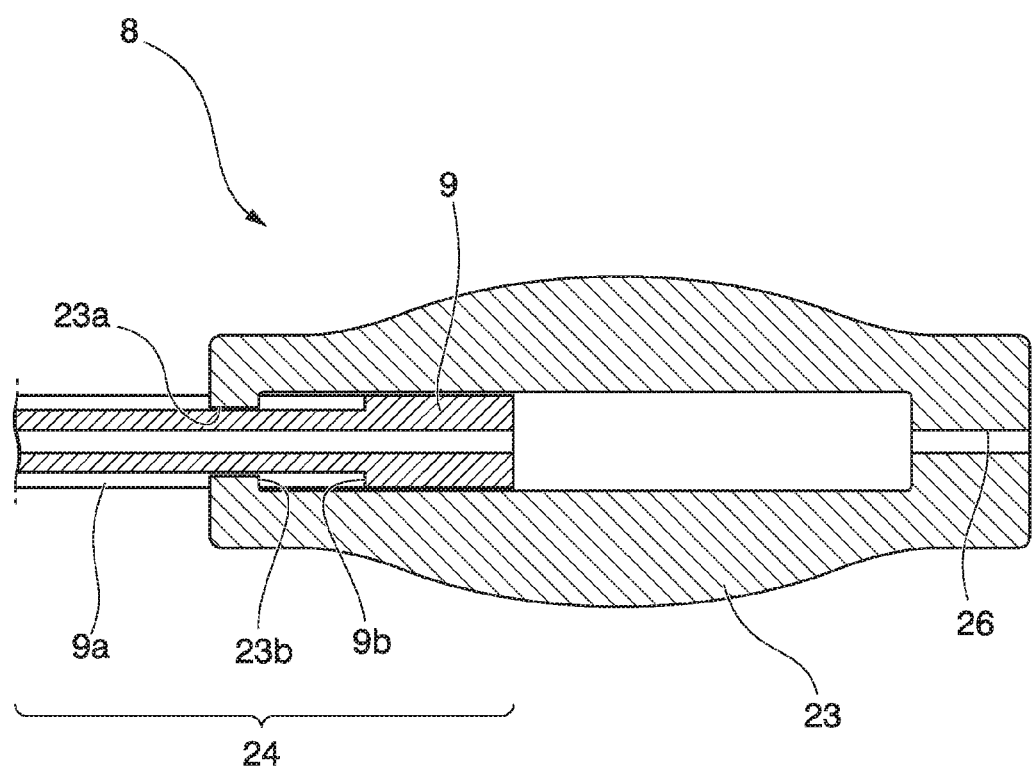
FIG. 7 is a schematic cross-sectional view of a manipulation section of the puncture needle for an endoscope.

The manipulation main body 9 has a lumen through which the needle tube 3 and the sheath 7 can be inserted. The attachment adaptor 18 is attached to the distal end of the manipulation main body 9. The proximal side of the manipulation main body 9 is inserted into the needle slider 23 formed in a tubular shape. The manipulation main body 9 and the attachment adaptor 18, and the manipulation main body 9 and the needle slider 23 are slidable in an axial direction while suppressing relative rotation around an axis as grooves, convex portions, or the like, (not show) formed in outer circumferential surfaces thereof are engaged with each other. Specifically, the needle slider 23 shown in FIG. 3 is provided to be movable in an axial direction of the manipulation main body 9 with respect to the manipulation main body 9. As shown in FIG. 7, the manipulation main body 9 slidably supports the needle slider 23 such that the needle slider 23 can move in the axial direction of the manipulation main body 9 in a state in which a convex portion 23a of the needle slider 23 is fitted into a concave portion 9a of the manipulation main body 9.

When the needle slider 23 is moved to the distal side of the manipulation main body 9, the needle slider 23 is configured to move to a position in contact with a stopper 61. In addition, the stopper 61 can move (advance) with respect to the manipulation main body 9 until abutting a diameter-increased portion (no reference numeral) of the distal end of the manipulation main body 9. For this reason, when the stopper 61 abuts the diameter-increased portion of the manipulation main body 9, the stopper 61 is configured such that the distal end of the needle tube 3 sufficiently protrudes from the distal end of the sheath 7 and a user causes the needle slider 23 to advance.

As shown in FIG. 7, the manipulation main body 9 and the needle slider 23 have a engaging structure 24 configured to restrict movement of the needle slider 23 to the proximal side of the manipulation main body 9. The engaging structure 24 is constituted by a needle slider engaging section (a engaging surface) 9b formed in the manipulation main body 9, and an abutting surface 23b formed at the convex portion 23a of the needle slider 23. The needle slider engaging section 9b and the abutting surface 23b come in contact with each other when the needle slider 23 is moved (retracted) to the most proximal side along the longitudinal axis of the manipulation main body 9 with respect to the manipulation main body 9. In a state in which the needle slider engaging section 9b and the abutting surface 23b come in contact with each other, the needle slider 23 is engaged to the manipulation main body 9 with respect to the longitudinal axis of the manipulation main body 9. When the needle slider 23 is moved to the proximal side of the manipulation main body 9, the needle slider 23 is configured to move to a position engaged by the engaging structure 24 shown in FIG. 7 (a position at which the abutting surface 23b of the convex portion 23a and the needle slider engaging section 9b of the manipulation main body 9 abut each other). When the needle slider 23 is locked to the manipulation main body 9 by the engaging structure 24, the proximal end of the inner sheath 74 is located closer to the proximal side than the needle tip 3a of the needle tube 3 in the internal space 72a of the coil body 72.

That is, the needle slider 23 can move from a first position engaged to the manipulation main body 9 to a second position that abuts the stopper 61 abutting the diameter-increased portion of the manipulation main body 9. In a process in which an operator moves the needle slider 23 between the first position and the second position, the distal end of the needle tube 3 is configured to protrude and withdraw from the distal end of the sheath 7.

The attachment adaptor 18 is movably connected to the manipulation main body 9 such that a protrusion amount of the sheath 7 from the distal end of the channel 107 of the ultrasonic endoscope 100 can be adjusted. The distal portion of the attachment adaptor 18 can be detachably attached to the proximal port member 107b of the ultrasonic endoscope 100.

The needle slider 23 is fixed to the proximal end of the needle tube 3. In addition, the needle slider 23 is connected to the manipulation main body 9 to be movable with respect to the manipulation main body 9.

Since the proximal side of the needle tube 3 protrudes from the proximal end of the sheath 7 to be fixed to the needle slider 23, the needle tube 3 can protrude or withdraw from the distal end of the sheath 7 as the needle slider 23 slides with respect to the manipulation main body 9.

Movement of the needle slider 23 shown in FIG. 3 is restricted by the stopper 61 such that the needle slider 23 can advance with respect to the manipulation main body 9 to only the position contact with the stopper 61. As the fixed position of the stopper 61 with respect to the manipulation main body 9 is adjusted, a maximum protrusion length from the sheath 7 of the needle tube 3 can be adjusted.

A state in which the needle slider 23 is present at a position to which the needle slider 23 moves to a limited position at the proximal side of the manipulation main body 9 is an initial state before use of the puncture needle 1. In the initial state, the distal end of the needle tube 3 is in the sheath 7. Specifically, the needle tip 3a of the needle tube 3 is located closer to the distal side than the proximal end of the inner sheath 74 in the internal space 72a of the coil body 72. In addition, in the embodiment, the distal end of the needle tube 3 is located between the proximal end 108b of the raising base 108 and the distal end of the bendable section 105.

The stylet 27 is attached to the proximal portion of the needle slider 23. The stylet 27 is a needle-shaped member inserted into the needle tube 3. The distal end of the stylet 27 is not limited to the needle shape but may have an end surface along a surface crossing the longitudinal axis of the stylet 27 or may have a curved surface such as a hemispherical surface or the like.

Figure 6:
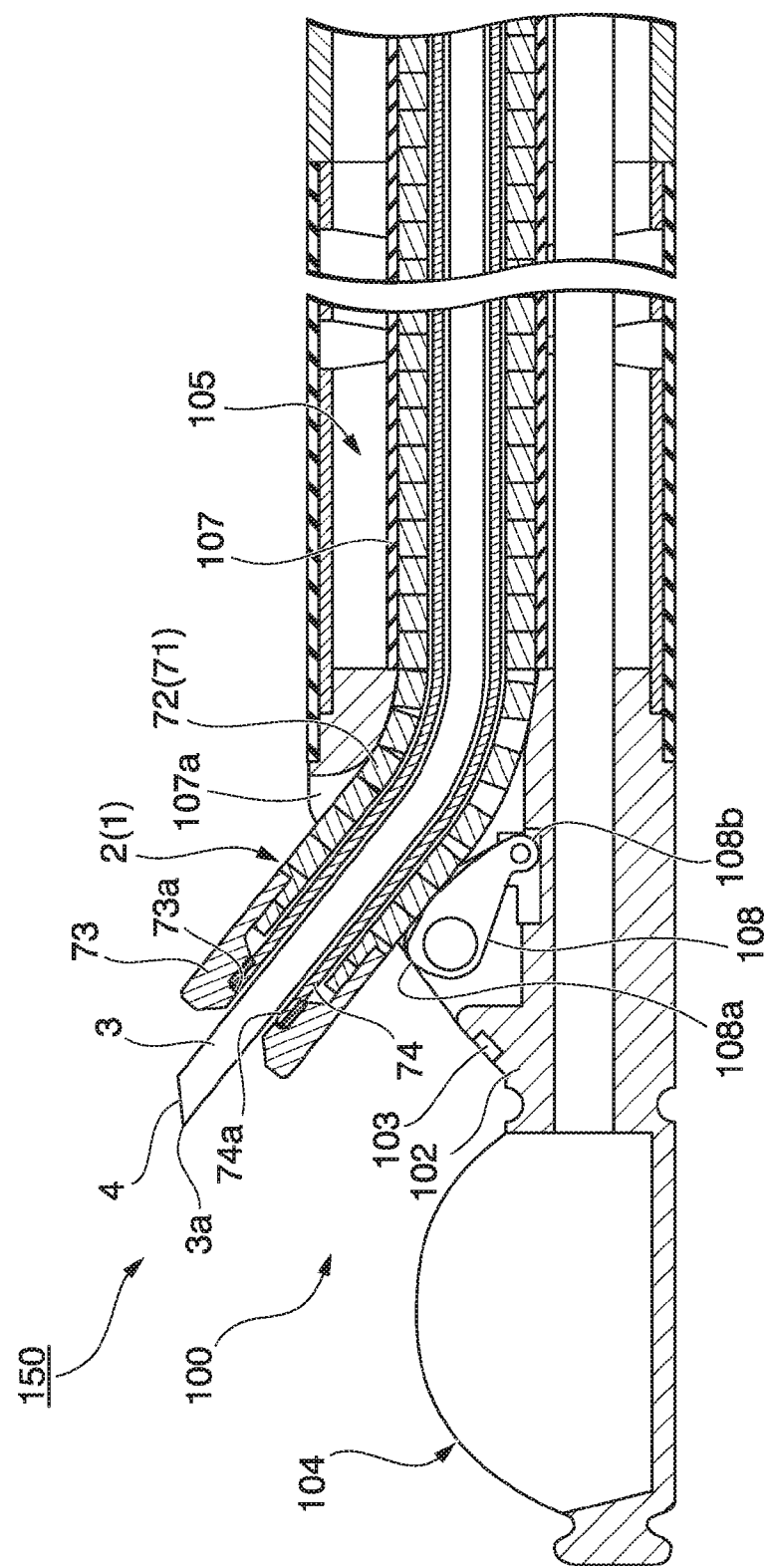
FIG. 6 is a view showing an action of the puncture needle for an endoscope.

Next, an action of the biopsy system 150 of the embodiment will be described. FIG. 6 is a view showing an action of the puncture needle 1.

Figure 8:
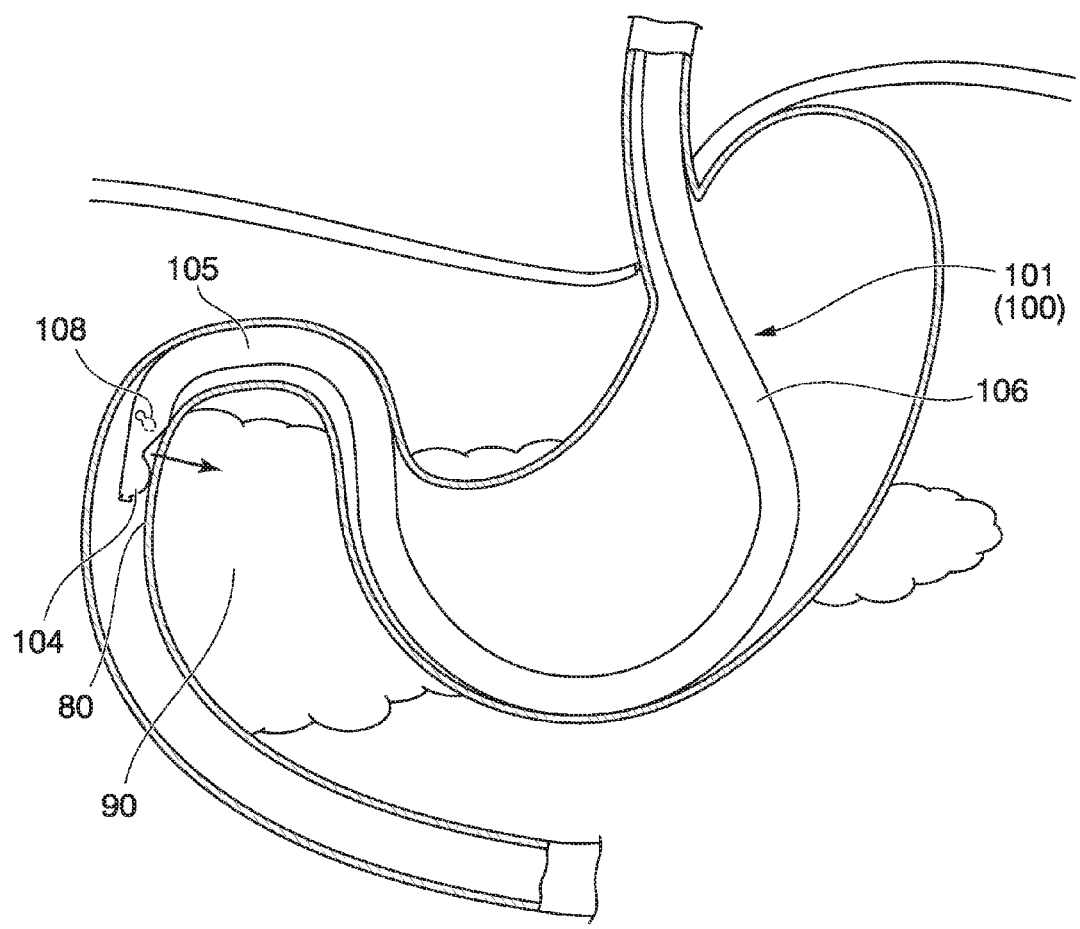
FIG. 8 is a schematic view showing an example of treatment in which the puncture needle for an endoscope is used with the endoscope.

In the biopsy system 150 (see FIG. 1) of the embodiment, as shown in FIG. 8, when the biopsy of the head of pancreas is performed using the ultrasonic endoscope 100, the bendable section 105 is bent to a level close to the limit of performance of the bendable section 105 of the ultrasonic endoscope 100 and the raising base 108 is also bent to a level close to the limit of performance. For this reason, since the puncture needle 1 passing through the channel 107 bent by the raising base 108 and the bendable section 105 is also largely bent, the coil body 72 of the outer sheath 71 that constitutes the puncture needle 1 is also largely bent. When the coil body 72 is moved until the distal end of the coil body 72 is located in the observation field of the optical observation unit 114 of the ultrasonic endoscope 100 while the coil body 72 is largely bent, the operator is in a state in which a distal end position of the coil body 72 can be identified on the monitor 116. In this state, the abutting surface 23b of the needle slider 23 is moved to a position abutting the needle slider engaging section 9b.

In this state, as shown in FIG. 5, the distal end of the inner sheath 74 is located closer to the distal side than the proximal end 108b of the raising base 108 in the coil body 72. In addition, in the same state, the proximal end of the inner sheath 74 is located closer to the proximal side than the needle tip 3a of the needle tube 3 in the internal space 72a of the coil body 72. Since the inner sheath 74 is disposed in the moving region of the needle tip 3a of the needle tube 3 in the internal space 72a of the coil body 72 bent by the raising base 108 or the bendable section 105 according to a positional relation, the needle tip 3a of the needle tube 3 can be prevented from being caught in the gap between the loops of the wire of the coil body 72 bent by the raising base 108 or the bendable section 105.

In addition, even when the coil body 72 is largely bent, since the coil body 72 can be moved such that the neighboring loops of the wire are separated while maintaining the cross-sectional shape of the inner sheath 74 in a substantially perfect circular state, the inner sheath 74 does not collapse.

Further, in the biopsy system 150 (see FIG. 1) of the embodiment, as shown in FIGS. 4 to 6, in the puncture needle 1, the needle tube 3 in the outer sheath 71 moves while coming in contact with the inner surface of the inner sheath 74 and not the inner surface of the coil body 72 of the outer sheath 71. Since the inner sheath 74 is formed of a resin, a frictional resistance between the needle tube 3 and the inner sheath 74 is smaller than that between metals. For this reason, in the embodiment, in comparison with the related art, the operation force required for movement of the needle tube 3 with respect to the sheath 7 may be reduced.

When the sheath 7 is disposed in the channel 107 formed in the bendable section 105 or at the raising base 108 of the ultrasonic endoscope 100, the sheath 7 is formed in a bent shape by the bendable section 105 or the raising base 108. The needle tube 3 passing through the sheath 7 is harder to move than when the sheath 7 is in a linear state as the frictional resistance between the sheath 7 and the needle tube 3 is increased at a portion in which the sheath 7 is bent and deformed. In the sheath 7 of the puncture needle 1 installed in the biopsy system 150 of the embodiment, since the inner sheath 74 formed of a resin is disposed in the coil body 72 formed of a metal, the operation force required for movement of the needle tube 3 in the portion at which the frictional resistance is increased due to the bending and deformation may be reduced in comparison with the case in which the inner sheath 74 is not provided. That is, according to the puncture needle 1 of the embodiment, the needle tube 3 can be moved according to an operator's intention with a light force even in a state in which the sheath 7 is bent and deformed.

In addition, in the embodiment, since the frictional resistance between the inner sheath 74 formed of a resin and the needle tube 3 formed of a metal is reduced, even when a difference between the inner diameter of the inner sheath 74 and the outer diameter of the needle tube 3 is reduced, the operation force required for movement of the needle tube 3 with respect to the sheath 7 may be reduced. For this reason, a gap in which the needle tube 3 meanders in the sheath 7 can be reduced, and followability of the distal portion of the needle tube 3 with respect to advancing or retracting manipulation of the needle tube 3 in the manipulation section 8 is good. That is, difficulty in transmission of the operation force from the proximal side to the distal side of the needle tube 3 due to meandering of the needle tube 3 in the inner sheath 74 can be prevented.

In addition, in the embodiment, since the needle tube 3 cannot easily meander in the inner sheath 74, when the needle tube 3 is to be moved to the distal side using the needle slider 23 of the manipulation section 8, bending of the needle tube 3 cannot be easily accumulated in the sheath 7 and movement of the distal end of the needle tube 3 can be efficiently performed. For this reason, push-back of the slider to the proximal side by a restoring force of linearly returning the needle tube in the meandering state, because the distal end of the needle tube is not moved even when the proximal portion of the needle tube is pushed to the distal slide by the slider, in the related art cannot easily occur in the biopsy system 150 according to the embodiment.

In addition, in the embodiment, the distal end 74a of the inner sheath 74 is fixed to the distal tip 73, and the distal tip 73 is further fixed to the distal portion of the coil body 72. For this reason, when the sheath 7 is deformed in the bent shape and the operation force from the proximal side to the distal side of the sheath 7 is transmitted to the distal side of the sheath 7, the distal tip 73 of the distal portion of the outer sheath 71 moves the inner sheath 74 in the coil body 72. For this reason, since the distal end of the inner sheath 74 does not move closer to the proximal side than the distal end of the outer sheath 71, the coil body 72 of the outer sheath 71 and the needle tube 3 do not come in direct contact with each other. In addition, since the portion other than the distal end 74a of the inner sheath 74 is not fixed to the outer sheath 71, flexibility of the outer sheath 71 cannot be easily lowered even when the inner sheath 74 is disposed in the outer sheath 71.

Further, the distal tip 73 may not be disposed at the distal portion of the outer sheath 71, and the distal end 74a of the inner sheath 74 may be directly fixed to the distal portion of the coil body 72 of the outer sheath 71. That is, a distal region of the inner sheath 74 raised by the raising base 108 may be directly or indirectly fixed to the coil body 72. In this case, the distal region has a fixing section fixed to the coil body 72. Further, the fixing section (also including a fixing section, which will be described below) employs a known fixing technique such as crimping, fusion bonding, fitting, binding, adhesion, soldering, brazing, welding, or the like. In the inner sheath 74, the region closer to the proximal side than the fixing section is relatively movable with respect to the coil body 72. Even in a state in which the proximal end of the inner sheath 74 is pulled and moved to the distal side of the coil body 72 according to raising of the coil body 72 by the raising base 108, the proximal end of the inner sheath 74 is located closer to the proximal side than the needle tip 3a of the needle tube 3 in the coil body 72.

In addition, the fixed position of the inner sheath 74 to the coil body 72 of the outer sheath 71 is not limited to the distal region of the inner sheath 74 but, for example, the proximal region of the inner sheath 74 extending closer to the proximal side of the coil body 72 than the needle tip 3a of the needle tube 3 may be directly or indirectly fixed to the coil body 72. In this case, the proximal region has a fixing region fixed to the coil body 72. A region of the inner sheath 74 closer to the distal side than the fixing section is relatively movable with respect to the coil body 72. Even in a state in which the distal end 74a of the inner sheath 74 is pulled and moved to the proximal side of the coil body 72 according to raising of the coil body 72 by the raising base 108, the distal end 74a of the inner sheath 74 is located closer to the distal side than the proximal end 108b of the raising base 108 in the coil body 72.

Further, the coil body 72 may be directly or indirectly fixed to an intermediate region of the inner sheath 74 between the needle tip 3a of the needle tube 3 and the proximal end 108b of the raising base 108. In this case, the intermediate region has a fixing section fixed to the coil body 72. In the inner sheath 74, a region closer to the distal side and a region closer to the proximal side than the fixing section are relatively movable with respect to the coil body 72. Even in a state in which the distal end 74a of the inner sheath 74 is pulled and moved to the proximal side of the coil body 72 according to raising of the coil body 72 by the raising base 108 and the proximal end 74b of the inner sheath 74 is pulled and moved to the distal side of the coil body 72, the distal end 74a of the inner sheath 74 is located closer to the distal side than the proximal end 108b of the raising base 108 in the coil body 72, and the proximal end 74b of the inner sheath 74 is located closer to the proximal side than the needle tip 3a of the needle tube 3 in the coil body 72.

As described above, even at any fixed position of the inner sheath 74, according to the bent shape of the coil body 72, the coil body 72 can be moved to separate the neighboring loops of the wire from each other while maintaining a cross-sectional shape of the inner sheath 74 in a substantially perfect circular state.

Further, when the inner diameter of the distal tip 73 is smaller than the outer diameter of the inner sheath 74, even though the distal end 74a of the inner sheath 74 is not fixed to the distal tip 73, if the inner sheath 74 is to be moved to the distal side of the coil body 72 with respect to the coil body 72, the distal end 74a of the inner sheath 74 abuts a proximal surface 73a of the distal tip 73. Even when the inner sheath 74 is to be moved to the proximal side of the coil body 72 with respect to the coil body 72, the proximal end 74b of the inner sheath 74 abuts a distal end of a restriction member 81 formed at the manipulation section 8. In the embodiment, the restriction member 81 is a substantially cylindrical member (see FIG. 4) fixed to an outer circumferential surface of the proximal region of the needle tube 3. Accordingly, the inner sheath 74 can restrict movement of the inner sheath 74 such that the inner sheath 74 does not escape from a region of the coil body 72 bent by the raising base 108 or the bendable section 105.

In the embodiment, the coil body 72 of the outer sheath 71 generates a gap between the neighboring loops of the wire that constitute the coil body 72 in a state in which the outer sheath 71 is bent by the raising base 108 and the bendable section 105. In particular, the gap between the loops of the wire generated by the raising base 108 remarkably affects slidability of the needle tube 3. In the embodiment, since the inner sheath 74 is disposed in the internal space 72a of the coil body 72 of the outer sheath 71, the gap between the loops of the wire of the coil body 72 is covered by the inner sheath 74. As a result, the needle tip 3a of the needle tube 3 that advances and retracts in the inner sheath 74 cannot easily caught in the gap between the loops of the wire of the coil body 72 even when the insertion body 2 is bent at a position of the raising base 108 or the bendable section 105.

Figure 9:
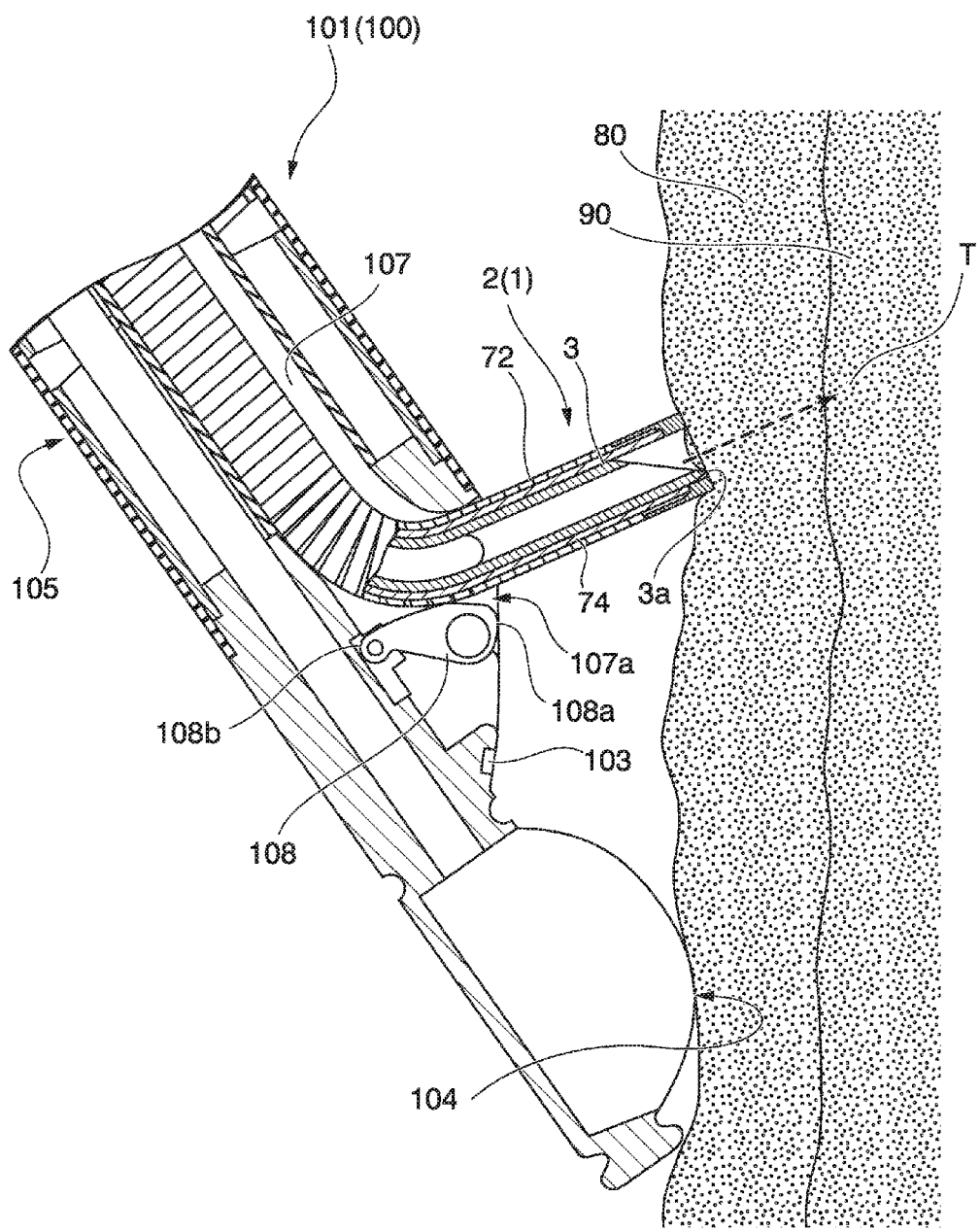
FIG. 9 is a schematic view showing a process of puncturing tissue using the puncture needle for an endoscope.

An example of a procedure using the puncture needle 1 of the embodiment is shown. FIG. 8 is a schematic view showing a process of a procedure of an exemplary biopsy. FIG. 9 is a schematic view showing an exemplary process of causing a needle tube to puncture tissue.

Hereinafter, an exemplary biopsy treatment in which the needle tube 3 of the puncture needle 1 is inserted into a lesion as a target tissue in a body and cells or the like of the lesion are collected through the needle tube 3 will be described. The procedure of the biopsy exemplified is an exemplary biopsy of the head of pancreas in the pancreas 90 shown in FIGS. 8 and 9. Further, an application target of the puncture needle 1 of the embodiment is not limited to a puncture into the head of pancreas for a biopsy.

First, an operator inserts the insertion section 101 of the ultrasonic endoscope 100 shown in FIG. 1 into the body, and introduces the distal portion of the insertion section 101 into the vicinity of the target tissue (in the embodiment, the head of pancreas) while observing the target tissue using the optical imaging mechanism 103 and appropriately bending the bendable section 105. After the introduction, the operator determines an area, in which a biopsy is performed, based on an observation result by the optical imaging mechanism 103 and the ultrasonic scanning mechanism 104. For example, when the biopsy of the head of pancreas is performed, the insertion section 101 is moved while maintaining a state in which the bendable section 105 is bent such that the optical imaging mechanism 103 and the ultrasonic scanning mechanism 104 disposed at the insertion section 101 of the ultrasonic endoscope 100 reach the duodenum 80.

When the biopsy of the head of pancreas is performed using the ultrasonic endoscope 100, in order to capture a puncture place of the puncture needle 1 in a field of vision of the ultrasonic endoscope 100, the bendable section 105 should be bent. In particular, when the biopsy of the head of pancreas is performed like the embodiment, the bendable section 105 is bent to a level near the limit of performance of the bendable section 105 of the ultrasonic endoscope 100, and the raising base 108 is also bent to a level near the limit of performance.

Next, the operator inserts the insertion body 2 of the puncture needle 1 into the channel 107 from the proximal port member 107b disposed at the operation section 109 of the ultrasonic endoscope 100 shown in FIG. 1. Then, the operator connects the attachment adaptor 18 of the manipulation section 8 to the proximal port member 107b. Accordingly, the manipulation section 8 of the puncture needle 1 is fixed to the ultrasonic endoscope 100 so as not to rotate with respect to the operation section 109.

For example, when back-cut processing is performed on the needle tube 3, a needle tip 3a cannot easily come in contact with the inner surface of the sheath 7. In addition, the needle tip 3a cannot easily come in contact with the inner surface of the sheath 7 similarly even when the needle tube 3 is, for example, a Menghini needle.

Next, the operator adjusts a protrusion amount of the sheath 7 from the distal end of the insertion section 101 of the ultrasonic endoscope 100 to an appropriate amount by loosening a fixing screw 10 (see FIG. 3) and relatively sliding the attachment adaptor 18 and the manipulation main body 9 while observing the sheath 7 and the inside of the body using the optical imaging mechanism 103 and the ultrasonic scanning mechanism 104. After adjustment, the operator fixes the protrusion amount of the sheath 7 by fastening the fixing screw 10. Here, the distal end of the coil body 72 is located in the observation field of the optical observation mechanism 103 of the ultrasonic endoscope 100, and the needle slider 23 is moved to the position abutting the needle slider engaging section 9b.

Next, the needle tube 3 is advanced with respect to the coil body 72 while the bendable section 105 is bent to a level near the limit of performance of the bendable section 105 of the ultrasonic endoscope 100 and the state in which the raising base 108 is also bent to a level near the limit of performance is maintained. Here, the coil body 72 of the outer sheath 71 is in the state in which the coil body 72 of the outer sheath 71 is bent by the raising base 108 and the bendable section 105, and the gap is generated between the loops of the wire that constitute the coil body 72. However, in the embodiment, the inner sheath 74 is disposed in the internal space of the coil body 72 of the outer sheath 71, and the gap between the loops of the wire of the coil body 72 is covered by the inner sheath 74 from the inside of the coil body 72. As a result, the needle tube 3 moving through the inner sheath 74 cannot be easily caught in the gap between the loops of the wire of the coil body 72 even when the insertion body 2 is bent in a state in which the coil body 72 is placed at the position of the raising base 108 or the bendable section 105.

Next, based on the observation result by the ultrasonic scanning mechanism 104, the stopper 61 is fixed to the manipulation main body 9 at a desired position by moving the stopper 61 in consideration of a distance to a target tissue T on which the biopsy is performed, and a maximum protrusion length of the needle tube 3 from the sheath 7 is adjusted.

In addition, as shown in FIG. 9, a protrusion direction of the insertion body 2 from a distal opening 107a of the channel 107 is set using the raising base 108 such that the needle tube 3 is pushed toward the position of the target tissue T. The raising base 108 deforms the sheath 7, the needle tube 3 and the stylet 27 in a bent shape by pressing the outer surface of the sheath 7. Further, in the embodiment, the stylet 27 may not be inserted through the needle tube 3. In the procedure of the biopsy of the head of pancreas according to the embodiment, the insertion body 2 is bent to a level near the limit of performance of the bendable section 105 or the raising base 108 of the ultrasonic endoscope 100.

Next, the operator advances the needle slider 23 shown in FIG. 3 to the distal side of the manipulation section 8. While the sheath 7 is bent by the raising base 108, since the needle tip 3a cannot be easily inserted into an inner surface of the inner sheath 74, the needle tube 3 is pushed by the needle slider 23 toward the distal end of the sheath 7.

When the needle tube 3 protrudes from the sheath 7 as shown in FIG. 9, the stylet 27 is returned into the needle tube 3. Accordingly, the needle tube 3 can puncture the tissue using the sharp needle tip 3a of the needle tube 3. Next, in a state in which the distal end of the sheath 7 abuts the intestinal wall, as the operator further advances the needle slider 23 to the distal side of the manipulation section 8, the needle tip 3a of the needle tube 3 protrudes from the distal end of the sheath 7 and punctures the tissue to be pushed to the target tissue T on which the biopsy is performed. Here, the stylet 27 is disposed in the needle tube 3 such that the tissue, which is not the biopsy target, does not enter the needle tube 3.

The operator can acquire positional information of the distal portion of the needle tube 3 entering in the tissue using the ultrasonic scanning mechanism 104. For this reason, the operator can observe an ultrasonic wave image showing an image of the distal portion of the needle tube 3 acquired in the ultrasonic scanning mechanism 104 using the ultrasonic observation unit 115 shown in FIG. 1. The operator causes the distal end (the needle tip 3a) of the needle tube 3 to reach the target tissue T on which the biopsy is performed with reference to the image of the distal portion of the needle tube 3 clearly projected to the ultrasonic observation unit 115.

In order to perform suction of the tissue into the needle tube 3, the operator extracts the stylet 27 from the insertion body 2 and the manipulation section 8. Accordingly, a through-hole extending from the distal end of the needle tube 3 to the proximal end of the needle slider 23 is generated. The operator connects a syringe or the like to a port 26 disposed at the proximal end of the needle slider 23 to suction the inside of the needle tube 3, and suctions and collects cells or the like of the target tissue T, on which the biopsy is performed, from the distal end of the needle tube 3.

When a necessary amount of cells or the like is completely collected, the needle tube 3 can be extracted from the tissue by retracting the needle slider 23 to the proximal side of the manipulation section 8, and the distal end of the needle tube 3 is accommodated in the sheath 7. When the needle tube 3 is extracted from the tissue, the attachment adaptor 18 is removed from the proximal port member 107b of the operation section 109 of the ultrasonic endoscope 100, and the puncture needle 1 is removed from the channel 107. Finally, the ultrasonic endoscope 100 is removed from a patient to terminate the series of treatments.

Second Embodiment

Figure 10:
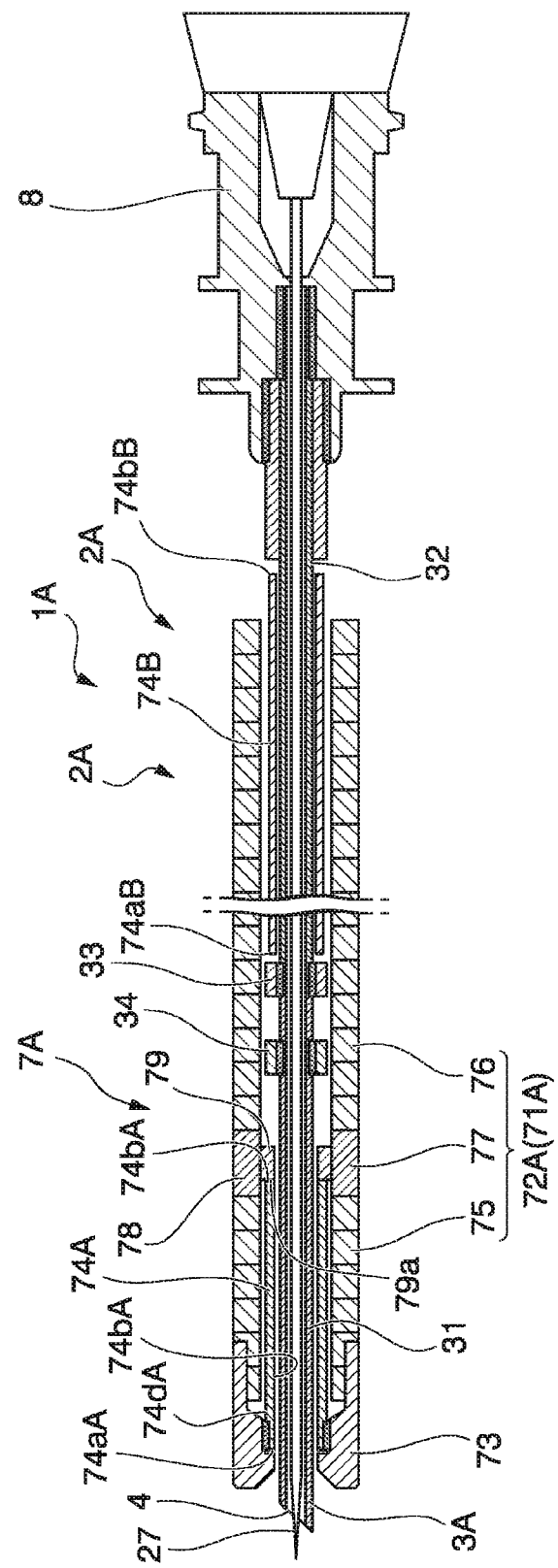
FIG. 10 is a schematic cross-sectional view of a puncture needle for an endoscope of a second embodiment of the present invention.
Figure 11:
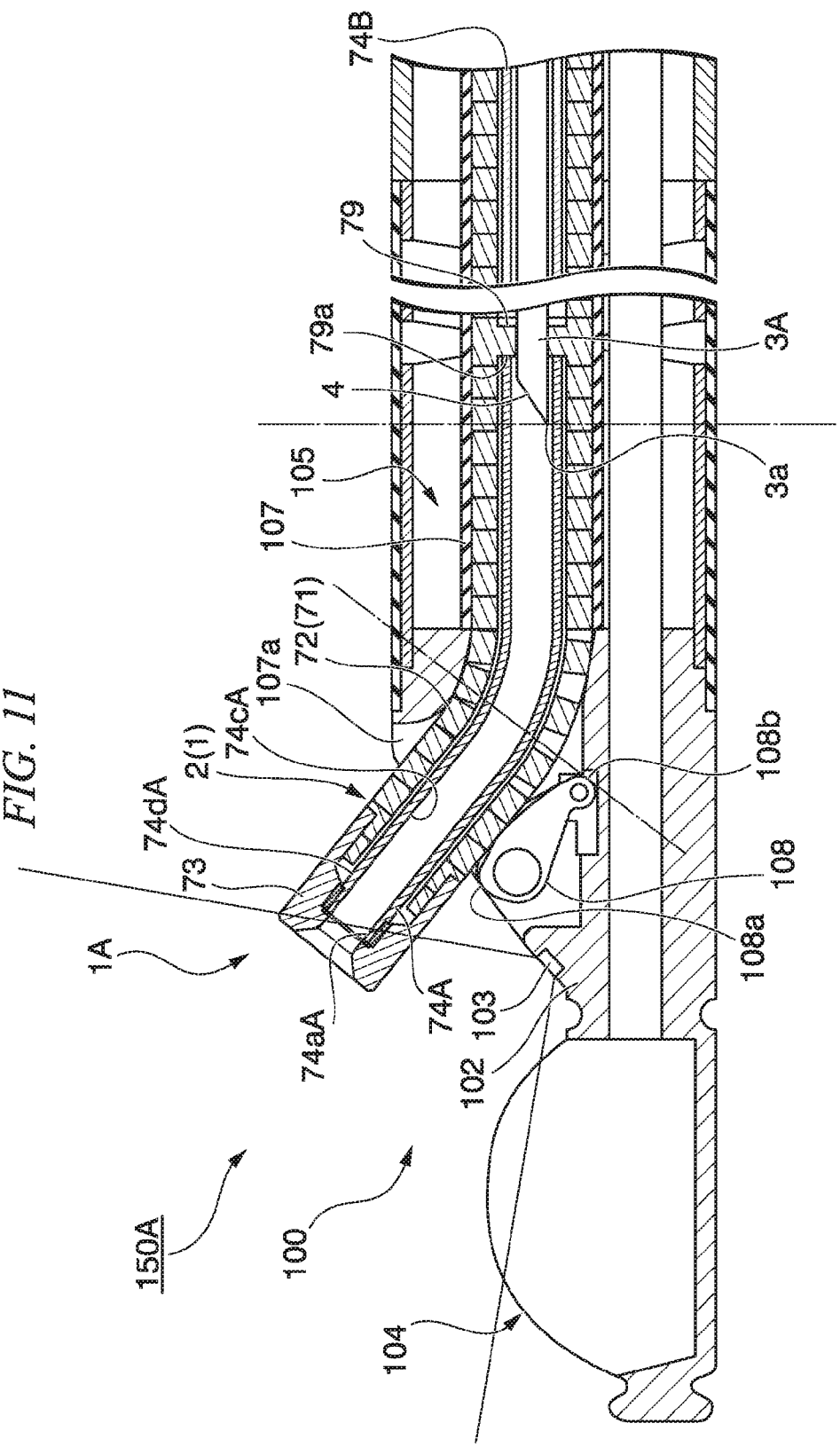
FIG. 11 is a cross-sectional view showing a state in which the puncture needle for an endoscope is combined with an endoscope.

A second embodiment of the present invention will be described. In the embodiment, the same components as disclosed in the first embodiment are designated by the same reference numerals as these of the first embodiment, and descriptions overlapping the first embodiment will be omitted. FIG. 10 is a schematic cross-sectional view of a puncture needle for an endoscope of the embodiment. FIG. 11 is a cross-sectional view showing a state in which the puncture needle for an endoscope is combined with an endoscope.

A biopsy system of the embodiment is distinguished from the first embodiment in that a puncture needle for an endoscope 1A (hereinafter, simply referred to as "a puncture needle 1A," see FIG. 10) having a configuration different from the puncture needle 1 of the biopsy system 150 of the first embodiment shown in FIG. 1 is provided.

The puncture needle 1A shown in FIG. 10 can be attached to the ultrasonic endoscope 100 (see FIG. 1) described in the first embodiment. As a structure in which the puncture needle 1A is attached to the ultrasonic endoscope 100, similar to the first embodiment, the attachment adaptor 18 is fixed to the proximal port member 107b. In addition, the structure of the manipulation section 8 is similar to the first embodiment.

As shown in FIG. 10, the puncture needle 1A includes an insertion body 2A having a configuration different from the insertion body 2 described in the first embodiment, instead of the insertion body 2 described in the first embodiment.

The insertion body 2A includes a needle tube 3A and a sheath 7A that have configurations different from the first embodiment.

The needle tube 3A may be a tubular metal member having a configuration different from the first embodiment, in which a distal side is relatively flexible and a proximal side is relatively hard.

In this case, the needle tube 3A includes a first tube 31, a second tube 32, a connecting tube 33 and a stopper 34.

The first tube 31 has the needle tip 3a having a sharp distal end that punctures tissue, similar to the opening 4 of the needle tube 3 described in the first embodiment.

The second tube 32 is a tubular member that is harder than the first tube 31. The first tube 31 and the second tube 32 are connected such that the first tube 31 and the second tube 32 are aligned coaxially and connected with each other by the connecting tube 33.

The connecting tube 33 is a tubular member into which a proximal end of the first tube 31 and a distal end of the second tube 32 are inserted. The connecting tube 33 is fixed to the first tube 31 and the second tube 32 by a known method such as welding, brazing, or the like.

The stopper 34 is a member fixed to an outer circumferential surface of the proximal portion of the first tube 31. The stopper 34 of the embodiment is a tubular member having an inner diameter which is substantially the same diameter as the outer diameter of the first tube 31, and an outer diameter that can come in contact with a protrusion 79 (to be described below) formed in the sheath 7A.

The sheath 7A is a tubular member having a configuration different from the first embodiment in which a distal side is relatively flexible and a proximal side is relatively hard. The relatively flexible distal portion of the sheath 7A corresponds to a region that is actively bent and deformed according to manipulation of the operation section 109 by a bendable mechanism constituted by the raising base 108 and the bendable section 105 of the ultrasonic endoscope 100. In the embodiment, the sheath 7A includes an outer sheath 71A, a first inner sheath 74A and a second inner sheath 74B. When the attachment adaptor 18 of the puncture needle 1A is attached to the proximal port member 107b of the ultrasonic endoscope 100, the distal end of the outer sheath 71A is located in a field of vision of the optical imaging mechanism 103, and the abutting surface 23b of the needle slider 23 is moved to a position abutting the needle slider engaging section 9b. In this state, as shown in FIG. 11, the distal end of the first inner sheath 74A (to be described below) is located closer to a distal side than the proximal end 108b of the raising base 108, and the proximal end of the first inner sheath 74A is located closer to a proximal side than the needle tip 3a of the needle tube 3. More specifically, in a state in which the distal end of the sheath 7A is located in a field of vision of the optical imaging mechanism 103, the first inner sheath 74A extends from the distal end of the sheath 7A to a region that arrives at a position of a proximal end 105b of the bendable section 105.

The outer sheath 71A includes a coil body 72A having a configuration different from the first embodiment, and the same distal tip 73 as the first embodiment.

The coil body 72A is a tubular metal member having a configuration in which a distal side is relatively flexible and a proximal side is relatively hard, and a wire is wound in a spiral shape.

Further, the coil body 72A may include a distal coil 75, a proximal coil 76 and a coil connecting member 77.

In this case, the distal coil 75 is a metal coil set to be more flexible than the proximal coil 76 and having different initial tensions at the distal coil 75 and the proximal coil 76 by a known method. A material that can be selected as a wire of the distal coil 75 is the same as that of the first embodiment.

The proximal coil 76 is a metal coil in which a diameter, a material, or the like, of the wire is adjusted such that the proximal coil 76 is relatively harder than the distal coil 75. A material that can be selected as a wire of the proximal coil 76 is similar to the first embodiment.

The coil connecting member 77 includes a tubular portion 78 into which a proximal end of the distal coil 75 and a distal end of the proximal coil 76 are inserted, and a protrusion 79 disposed in the tubular portion 78. In the embodiment, the tubular portion 78 and the protrusion 79 are integrally formed with each other.

The protrusion 79 is a portion engaged with the stopper 34 to restrict movement of the first tube 31 of the needle tube 3A such that the stopper 34 of the needle tube 3A cannot pass from the proximal side to the distal side of the protrusion 79. The protrusion 79 prevents the first tube 31 from being removed from the distal end of the sheath 7A when the first tube 31 and the second tube 32 are unintentionally separated.

The first inner sheath 74A is a tubular member having a distal end 74aA and a proximal end 74bA. The first inner sheath 74A is formed of a resin in consideration of reduction in sliding resistance between the needle tube 3A and the first inner sheath 74A, like the inner sheath 74 described in the first embodiment. Like the first embodiment, the first inner sheath 74A is also substantially disposed coaxially with a central axis of the coil body 72A in the coil body 72A. In addition, the first inner sheath 74A has an inner circumferential surface 74cA and an outer circumferential surface 74dA, and the inner circumferential surface 74cA has an insertion path into which the needle tube 3A can be inserted. The outer circumferential surface 74dA covers the gap between the loops of the wire generated when the coil body 72A (the distal coil 75) is bent between the distal end 74aA and the proximal end 74bA of the first inner sheath 74A from the inside of the coil body 72A (the distal coil 75). Further, since the first inner sheath 74A is disposed over between the neighboring loops of the wire of the coil body 72A (the distal coil 75) in the coil body 72A, the first inner sheath 74A functions as a cover member configured to cover the gap between the loops of the wire. In addition, the first inner sheath 74A covers a clearance between the outer sheath 71A and the needle tube 3A to prevent meandering of the needle tube 3A. The first inner sheath 74A of the embodiment may be a tubular member formed of, for example, polyetheretherketone (PEEK) in order to prevent the inner surface of the first inner sheath 74A from being damaged by the sharp distal end of the needle tube 3.

Like the first embodiment, the distal end 74aA of the first inner sheath 74A is fixed to the distal tip 73.

The proximal end 74bA of the first inner sheath 74A extends to the vicinity of a distal surface 79a of the protrusion 79 of the coil connecting member 77. A portion in the entire length of the first inner sheath 74A closer to the proximal side than a fixing place of the first inner sheath 74A and the distal tip 73 is slidable with respect to the distal coil 75. Further, like the first embodiment, the distal tip 73 may not be disposed at the distal portion of the outer sheath 71A, and the distal end 74a of the inner sheath 74A may be directly fixed to the distal portion of the coil body 72A (the distal coil 75) of the outer sheath 71A. That is, like the first embodiment, a distal region of the first inner sheath 74A raised by the raising base 108 may be directly or indirectly fixed to the coil body 72 (the distal coil 75). In this case, the distal region has a fixing section fixed to the coil body 72A (the distal coil 75). A region of the first inner sheath 74A closer to the proximal side than the fixing section is relatively movable with respect to the coil body 72A. Even in a state in which the proximal end 74bA of the first inner sheath 74A is pulled and moved to the distal side of the coil body 72A according to raising of the coil body 72 by the raising base 108, the proximal end 74bA of the first inner sheath 74A is located closer to the proximal side than the needle tip 3a of the needle tube 3 in the coil body 72A (the distal coil 75).

In addition, a fixed position of the first inner sheath 74A to the coil body 72A of the outer sheath 71A is not limited to the distal region of the first inner sheath 74A but, for example, a proximal region of the first inner sheath 74A extending closer to the proximal side of the coil body 72A than the needle tip 3a of the needle tube 3 may be directly or indirectly fixed to the coil body 72A (the distal coil 75). For example, the proximal region may be fixed to the protrusion 79 to be indirectly fixed to the coil body 72 (the distal coil 75). In this case, the proximal region has a fixing section fixed to the coil body 72A (the distal coil 75). A region of the first inner sheath 74A closer to the distal side than the fixing section is relatively movable with respect to the coil body 72A. Even in a state in which the distal end 74aA of the first inner sheath 74A is pulled and moved to the proximal side of the coil body 72A according to raising of the coil body 72A (the distal coil 75) by the raising base 108, the distal end 74aA of the first inner sheath 74A is located closer to the distal side than the proximal end 108b of the raising base 108 in the coil body 72A (the distal coil 75).

Further, the coil body 72A (the distal coil 75) may be directly or indirectly fixed to an intermediate region of the first inner sheath 74A between the needle tip 3a of the needle tube 3 and the proximal end of the raising base 108. In this case, the intermediate region has a fixing section fixed to the coil body 72A (the distal coil 75). In the first inner sheath 74A, a region closer to the distal side and a region closer to the proximal side than the fixing section are relatively movable with respect to the coil body 72A. Even in a state in which the distal end 74aA of the first inner sheath 74A is pulled and moved to the proximal side of the coil body 72A according to raising of the coil body 72A (the distal coil 75) by the raising base 108 and the proximal end 74bA of the first inner sheath 74A is pulled and moved to the distal side of the coil body 72A, the distal end 74aA of the first inner sheath 74 is located closer to the distal side than the proximal end 108b of the raising base 108 in the coil body 72A, and the proximal end 74bA of the first inner sheath 74A is located closer to the proximal side than the needle tip 3a of the needle tube 3 in the coil body 72A (the distal coil 75).

As described above, even in any fixed position of the inner sheath 74, the coil body 72A (the distal coil 75) can be moved such that the neighboring loops of the wire are separated while maintaining a cross-sectional shape of the first inner sheath 74A in a substantially perfect circular state according to the bent shape of the coil body 72A.

In addition, in the case in which the inner diameter of the distal tip 73 is smaller than the outer diameter of the first inner sheath 74A, even though the distal end 74aA of the first inner sheath 74A is not fixed to the distal tip 73, when the first inner sheath 74A is to be moved to the distal side of the coil body 72A with respect to the coil body 72A, the distal end 74aA of the first inner sheath 74A abuts the distal tip 73. Even when the first inner sheath 74A is to be moved to the proximal side of the coil body 72A with respect to the coil body 72A, the proximal end 74bA of the first inner sheath 74A abuts the distal surface 79a of the protrusion 79. Accordingly, the inner sheath 74 can restrict movement of the inner sheath 74 so as not to escape from a region of the coil body 72A (the distal coil 75) bent by the raising base 108 or the bendable section 105.

The second inner sheath 74B is a tubular member having a distal end 74aB and a proximal end 74bB. The second inner sheath 74B is disposed closer to the proximal side than the protrusion 79 of the coil connecting member 77 in the outer sheath 71A. The distal end 74aB of the second inner sheath 74B is disposed to the proximal side to be distant from the protrusion 79 of the coil connecting member 77 so as not to interfere with the stopper of the needle tube 3A. The proximal end 74bB of the second inner sheath 74B is fixed to the same manipulation section 8 as the first embodiment. Further, the proximal end 74bB of the second inner sheath 74B may be not fixed to the manipulation section 8. For example, the second inner sheath 74B is fixed to the needle tube 3A (the second tube 32).

The second inner sheath 74B covers a clearance between the outer sheath 71A and the needle tube 3A to prevent meandering of the needle tube 3A. Since the second inner sheath 74B is disposed in a region that does not come in contact with the sharp distal end of the needle tube 3A, there is no need to select a material for the purpose of protecting the second inner sheath 74B from the sharp distal end of the needle tube 3A. The second inner sheath 74B may be formed of a material to reduce a sliding resistance with respect to the outer sheath 71A and the needle tube 3A.

The insertion body 2A of the puncture needle 1A of the embodiment is connected to the manipulation section 8 described in the first embodiment. That is, in the embodiment, the proximal end of the proximal coil 76 of the outer sheath 71A is fixed to the manipulation section 8.

Next, an action of the puncture needle 1A of the embodiment will be described.

The needle tube 3A of the embodiment has different mechanical characteristics differing between the distal side and the proximal side as the first tube 31 and the second tube 32 are connected by the connecting tube 33. A distal side in the entire length of the needle tube 3A is flexible to be easily deformed in a bent shape by the bendable mechanism (the bendable section 105 and the raising base 108), and a proximal side in the entire length of the needle tube 3A is hard such that the operation force from the manipulation section 8 is efficiently transmitted to the distal end of the needle tube 3A.

Like the first embodiment, a frictional resistance between the first inner sheath 74A and the needle tube 3A is smaller than that between metals. In addition, a frictional resistance between the second inner sheath 74B and the needle tube 3A is smaller than that between metals. In this way, in the embodiment, a sliding resistance when the needle tube 3A advances and retracts in the sheath 7A is reduced substantially throughout the length of the sheath 7A.

In addition, when the attachment adaptor 18 of the puncture needle 1A is attached to the proximal port member 107b of the ultrasonic endoscope 100, the protrusion 79 is disposed closer to the proximal side than the proximal end 105b of the bendable section 105. For this reason, a region between the first inner sheath 74A and the second inner sheath 74B is also disposed closer to the proximal side than the proximal end 105b of the bendable section 105 when the attachment adaptor 18 of the puncture needle 1A is attached to the proximal port member 107b of the ultrasonic endoscope 100. In addition, in the entire length of the sheath 7A, since a clearance between the coil body 72A of the outer sheath 71A and the needle tube 3A is provided between the first inner sheath 74A and the second inner sheath 74B, an increase in sliding resistance between the coil body 72A and the needle tube 3A when the sheath 7A is bent cannot easily occur.

In addition, in a state in which the attachment adaptor 18 of the puncture needle 1A is attached to the proximal port member 107b of the ultrasonic endoscope 100, the operator adjusts the outer sheath 71A such that the distal end of the outer sheath 71A is located in a field of vision of the optical imaging mechanism 103. Here, the needle slider 23 is in a state in which the abutting surface 23b of the needle slider 23 is moved to the position abutting the needle slider engaging section 9b. In this state, as shown in FIG. 11, the distal end 74aA of the first inner sheath 74A is located closer to the distal side than the proximal end 108b of the raising base 108, and the proximal end 74bA of the first inner sheath 74A is located closer to the proximal side than the needle tip 3a of the needle tube 3.

In the embodiment, in the coil body 72A (the distal coil 75) of the outer sheath 71A, in a state in which the outer sheath 71A is bent by the raising base 108 and the bendable section 105, a gap between the neighboring loops of the wire that constitute the coil body 72A is generated. In the embodiment, since the first inner sheath 74A is disposed in the coil body 72A (the distal coil 75) of the outer sheath 71A, the gap between the loops of the wire of the coil body 72A is covered by the first inner sheath 74A. As a result, the needle tip 3a of the needle tube 3 that advances and retracts in the first inner sheath 74A cannot be easily caught in the gap between the loops of the wire of the coil body 72A even when the insertion body 2 is bent at a position of the raising base 108 or the bendable section 105.

Hereinabove, while the embodiments of the present invention have been described in detail with reference to the accompanying drawings, specific configurations are not limited to the embodiments but may include design changes without departing from the spirit of the present invention.

For example, in the first and second embodiments, the inner sheath (the first inner sheath) may be disposed only in a region which is considered as a region of the entire length of the sheath to be deformed in a bent shape by the raising base. In addition, in the first and second embodiments, the inner sheath (the first inner sheath) may be disposed in a region only in which the entire length of the sheath is considered to be deformed in a bent shape by the raising base and the bendable section.

In addition, in the second embodiment, the needle tube 3A or/and the coil body 72A may be substituted with the needle tube 3 or/and the coil body 72 corresponding to the first embodiment.

In addition, the components shown in the above-mentioned embodiments may be appropriately combined with each other.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

What is claimed is:

1. A puncture needle for an endoscope used with the endoscope having a treatment tool insertion channel and a bendable section which is provided closer to a distal end of the endoscope than a proximal end of the endoscope, a raising base configured to raise a treatment tool inserted through the channel, and an observation optical system, the puncture needle for the endoscope comprising:
   a coil sheath having an outer diameter that is capable of being inserted into the treatment tool insertion channel and constituted by a wire wound as a coil shape along a longitudinal axis thereof;
   a needle tube having a needle tip formed at a distal end thereof and movable along the longitudinal axis of the coil sheath inside the coil sheath, the needle tube being a tubular member;
   a manipulation section provided at a proximal portion of the coil sheath;
   a needle slider disposed at the manipulation section, configured to advance and retract the needle tube by advance and retract manipulation with respect to the manipulation section, and connected to a proximal end of the needle tube;
   the manipulation section comprising a needle slider engaging section configured to engage the needle slider so that the needle slider engaging section restricts retracting of the needle slider; and
   an inner sheath having a proximal end, a distal end positioned in the coil sheath, an outer circumferential surface configured to cover a gap between neighboring loops of the wire of the coil sheath from inside of the coil sheath elongated between the distal end of the inner sheath and the proximal end of the inner sheath, and an inner circumferential surface configured to form an insertion path into which the needle tube is configured to be inserted, wherein,
   the needle slider having an abutting surface that is configured to abut the needle slider engaging section when the needle slider moves backwards,
   in a state where a distal end of the coil sheath is located in an observation field of the observation optical system and a proximal end of the coil sheath is located closer to the proximal end of the endoscope than a proximal end of the raising base, when the needle tip is located closer to the proximal end of the coil sheath than the distal end of the inner sheath and the proximal end of the raising base, and the needle tip is located closer to the distal end of the coil sheath than a distal end of the bendable section, the abutting surface of the needle slider is configured to abut the needle slider engaging section.

2. The puncture needle for an endoscope according to claim 1, wherein
   the distal end of the inner sheath is fixed to the distal end of the coil sheath at a fixed portion of the inner sheath, and
   the inner sheath is slidable with respect to the coil sheath in an entire region of the inner sheath closer to the proximal end of the inner sheath than the fixed portion of the inner sheath.

3. The puncture needle for an endoscope according to claim 1, wherein the coil sheath has:
   a metal coil body through which the inner sheath and the needle tube are inserted;
   a tubular distal tip fixed to a distal end of the coil body, having an inner diameter smaller than that of the coil body and through which the needle tube is capable of being inserted; and
   a protrusion protruding further inward than an inner surface of the coil body at a position distant from the distal end of the coil body to the proximal side, and
   the inner sheath is disposed between the distal tip and the protrusion, and advance and retract movement in a direction along a centerline of the coil body is restricted by the distal tip and the protrusion.

4. The puncture needle for an endoscope according to claim 3, wherein the coil body is a coil having a metal wire that are exposed to an outer surface of the coil sheath, and the inner sheath is attached to an inner surface of the coil body to cover the inner surface of the coil body throughout the circumference when seen in a cross-section perpendicular to the centerline of the coil body.

5. The puncture needle for an endoscope according to claim 1, wherein the raising base comes in contact with the coil sheath at a distal end of the treatment tool insertion channel to deflect the distal end of the coil sheath.

6. The puncture needle for an endoscope according to claim 5, wherein the bendable section has a plurality of connected joints configured to bend the treatment tool insertion channel, and is formed closer to the proximal end of the endoscope than the raising base.

7. The puncture needle for an endoscope according to claim 1, wherein
the inner sheath has a distal region raised by the raising base,
the distal region of the inner sheath raised by the raising base has a fixing section fixed to the coil sheath,
a region of the inner sheath closer to the proximal end thereof than the fixing section of the distal region of the inner sheath raised by the raising base is movable with respect to the coil sheath, and
when the proximal end of the inner sheath is moved toward the distal end of the coil sheath in response to raising of the coil sheath by the raising base, the proximal end of the inner sheath is located closer to the proximal end of the endoscope than the needle tip of the needle tube in the coil sheath.

8. The puncture needle for an endoscope according to claim 1, wherein
the inner sheath has a proximal region extending closer to the proximal end of the coil sheath than the needle tip of the needle tube,
the proximal region of the inner sheath has a fixing section fixed to the coil sheath,
a region of the inner sheath closer to the distal end of the inner sheath than the fixing section of the proximal region of the inner sheath is movable with respect to the coil sheath, and
when the distal end of the inner sheath is moved toward the proximal end of the coil sheath in response to raising of the coil sheath by the raising base, the distal end of the inner sheath is located closer to the distal end of the coil sheath than the proximal end of the raising base in the coil sheath.

9. The puncture needle for an endoscope according to claim 1, wherein
the inner sheath has an intermediate region disposed between the needle tip of the needle tube and the proximal end of the raising base,
the intermediate region of the inner sheath has a fixing section fixed to the coil sheath,
in the inner sheath, a region of the inner sheath closer to the distal end of the inner sheath than the fixing section of the intermediate region of the inner sheath and a region closer to the proximal end of the inner sheath than the fixing section of the intermediate region of the inner sheath are movable with respect to the coil sheath, and
when the distal end of the inner sheath is moved toward the proximal end of the coil sheath in response to raising of the coil sheath by the raising base, and the proximal end of the inner sheath is moved toward the distal end of the coil sheath, the distal end of the inner sheath is located closer to the distal end of the coil sheath than the proximal end of the raising base in the coil sheath, and the proximal end of the inner sheath is located closer to the proximal end of the coil sheath than the needle tip of the needle tube in the coil sheath.

10. The puncture needle for an endoscope according to claim 1, wherein
an attachment adaptor that is configured so as to be attached to the endoscope is provided in a distal end portion of the manipulation section, the distal end portion of the manipulation section being closer to a distal end of the manipulation section than a proximal end of the manipulation section,
the attachment adaptor is also configured to be attached to the manipulation section and is movable in an axial direction of the manipulation section with respect to the manipulation section,
the needle slider is attached to a proximal end portion of the manipulation section so as to be movable in the axial direction with respect to the manipulation section, the proximal end portion of the manipulation section being closer to the proximal end of the manipulation section than the distal end of the manipulation section, and
in a state where the attachment adaptor is attached to the endoscope and the abutting surface of the needle slider abuts the needle slider engaging section, the needle tip is located closer to the proximal end of the coil sheath than the distal end of the inner sheath and the proximal end of the raising base, and the needle tip is located closer to the distal end of the coil sheath than the distal end of the bendable section.

11. The puncture needle for an endo scope according to claim 1, further comprising a stylet configured to be movable in the axial direction and provided in the needle tube, the stylet being configured to protrude from the needle tip.

12. The puncture needle for an endoscope according to claim 10, wherein
the distal end of the inner sheath is fixed to the distal end of the coil sheath at a fixed portion of the inner sheath, and
the inner sheath is slidable with respect to the coil sheath in an entire region of the inner sheath closer to the proximal end of the inner sheath than the fixed portion of the inner sheath.

13. The puncture needle for an endoscope according to claim 10, wherein
the inner sheath has a distal region raised by the raising base,
the distal region of the inner sheath raised by the raising base has a fixing section fixed to the coil sheath,
a region of the inner sheath closer to the proximal end thereof than the fixing section of the distal region of the inner sheath raised by the raising base is movable with respect to the coil sheath, and
when the proximal end of the inner sheath is moved toward the distal end of the coil sheath in response to raising of the coil sheath by the raising base, the proximal end of the inner sheath is located closer to the proximal end of the endoscope than the needle tip of the needle tube in the coil sheath.

14. The puncture needle for an endoscope according to claim 10, wherein
the inner sheath has a proximal region extending closer to the proximal end of the coil sheath than the needle tip of the needle tube,
the proximal region of the inner sheath has a fixing section fixed to the coil sheath, a region of the inner sheath closer to the distal end of the inner sheath than the fixing section of the proximal region of the inner sheath is movable with respect to the coil sheath, and when the distal end of the inner sheath is moved toward the proximal end of the coil sheath in response to raising of the coil sheath by the raising base, the distal end of the inner sheath is located closer to the distal end of the coil sheath than the proximal end of the raising base in the coil sheath.

15. The puncture needle for an endoscope according to claim 10, wherein the inner sheath has an intermediate region disposed between the needle tip of the needle tube and the proximal end of the raising base, the intermediate region of the inner sheath has a fixing section fixed to the coil sheath, in the inner sheath, a region of the inner sheath closer to the distal end of the inner sheath than the fixing section of the intermediate region of the inner sheath, and a region closer to the proximal end of the inner sheath than the fixing section of the intermediate region of the inner sheath are movable with respect to the coil sheath, and when the distal end of the inner sheath is moved toward the proximal end of the coil sheath in response to raising of the coil sheath by the raising base, and the proximal end of the inner sheath is moved toward the distal end of the coil sheath, the distal end of the inner sheath is located closer to the distal end of the coil sheath than the proximal end of the raising base in the coil sheath, and the proximal end of the inner sheath is located closer to the proximal end of the coil sheath than the needle tip of the needle tube in the coil sheath.

16. The puncture needle for an endoscope according to claim 11, wherein the distal end of the inner sheath is fixed to the distal end of the coil sheath at a fixed portion fixed to the coil sheath, and the inner sheath is slidable with respect to the coil sheath in an entire region of the inner sheath closer to the proximal end of the inner sheath than the fixed portion of the inner sheath.

17. The puncture needle for an endoscope according to claim 11, wherein the inner sheath has a distal region raised by the raising base, the distal region of the inner sheath raised by the raising base has a fixing section fixed to the coil sheath, a region of the inner sheath closer to the proximal end thereof than the fixing section of the distal region of the inner sheath raised by the raising base is movable with respect to the coil sheath, and when the proximal end of the inner sheath is moved toward the distal end of the coil sheath in response to raising of the coil sheath by the raising base, the proximal end of the inner sheath is located closer to the proximal end of the endoscope than the needle tip of the needle tube in the coil sheath.

18. The puncture needle for an endoscope according to claim 11, wherein the inner sheath has a proximal region extending closer to the proximal end of the coil sheath than the needle tip of the needle tube, the proximal region of the inner sheath has a fixing section fixed to the coil sheath, a region of the inner sheath closer to the distal end of the inner sheath than the fixing section of the proximal region of the inner sheath is movable with respect to the coil sheath, and when the distal end of the inner sheath is moved toward the proximal end of the coil sheath in response to raising of the coil sheath by the raising base, the distal end of the inner sheath is located closer to the distal end of the coil sheath than the proximal end of the raising base in the coil sheath.

19. The puncture needle for an endoscope according to claim 11, wherein the inner sheath has an intermediate region disposed between the needle tip of the needle tube and the proximal end of the raising base, the intermediate region of the inner sheath has a fixing section fixed to the coil sheath, in the inner sheath, a region of the inner sheath closer to the distal end of the inner sheath than the fixing section of the intermediate region of the inner sheath and a region closer to the proximal end of the inner sheath than the fixing section of the intermediate region of the inner sheath are movable with respect to the coil sheath, and when the distal end of the inner sheath is moved toward the proximal end of the coil sheath in response to raising of the coil sheath by the raising base, and the proximal end of the inner sheath is moved toward the distal end of the coil sheath, the distal end of the inner sheath is located closer to the distal end of the coil sheath than the proximal end of the raising base in the coil sheath, and the proximal end of the inner sheath is located closer to the proximal end of the coil sheath than the needle tip of the needle tube in the coil sheath.

\* \* \* \* \*